US007885793B2

(12) United States Patent
Padmanabhan

(10) Patent No.: US 7,885,793 B2
(45) Date of Patent: Feb. 8, 2011

(54) METHOD AND SYSTEM FOR DEVELOPING A CONCEPTUAL MODEL TO FACILITATE GENERATING A BUSINESS-ALIGNED INFORMATION TECHNOLOGY SOLUTION

(75) Inventor: Harirajan Padmanabhan, Overland Park, KS (US)

(73) Assignee: International Business Machines Corporation, Armonk, NY (US)

( * ) Notice: Subject to any disclaimer, the term of this patent is extended or adjusted under 35 U.S.C. 154(b) by 848 days.

(21) Appl. No.: 11/751,951

(22) Filed: May 22, 2007

(65) Prior Publication Data

US 2008/0294408 A1 Nov. 27, 2008

(51) Int. Cl.
*G06F 17/50* (2006.01)
*G06F 9/44* (2006.01)

(52) U.S. Cl. .............................. 703/2; 703/22; 703/24; 705/5; 705/7; 370/229

(58) Field of Classification Search .................... 703/2, 703/22-24; 705/5, 7; 370/229
See application file for complete search history.

(56) References Cited

U.S. PATENT DOCUMENTS 6,615,166 B1 * 9/2003 Guheen et al. ................ 703/27
6,957,186 B1 * 10/2005 Guheen et al. ............... 705/1.1
7,149,698 B2 * 12/2006 Guheen et al. ............... 705/1.1
7,315,826 B1 * 1/2008 Guheen et al. ................. 705/7
2004/0006566 A1 * 1/2004 Taylor et al. ................ 707/100
2005/0203784 A1 9/2005 Rackham
2006/0129419 A1 6/2006 Flaxer et al.
2006/0150143 A1 7/2006 Andreev et al.
2006/0235732 A1 * 10/2006 Miller et al. ................... 705/7

OTHER PUBLICATIONS

OMG Model Driven Architecture; 1997-2007 Object Management Group, Inc.; 2 pages.
Rechtin, Eberhardt; Systems Architecting Creating and Building Complex Systems; 1991 Prentice-Hall Inc; pp. 1 and 14-25.

* cited by examiner

*Primary Examiner*—Thai Phan
(74) *Attorney, Agent, or Firm*—Schmeiser, Olsen & Watts; John R. Pivnichy

(57) ABSTRACT

A method and system for developing a conceptual model to facilitate generating a business-aligned information technology (IT) solution. Requirements of the IT solution are defined. A conceptual model is developed by business and IT stakeholders. The conceptual model represents an IT solution design and includes systems, conceptual components and operational concepts. The conceptual components represent hardware components and software components of the IT solution. The operational concepts indicate interactions among the conceptual components that are needed to perform business functions. A computing system generates documentation of the conceptual model. The documentation is available and accessible to the business and IT stakeholders and includes documentation of the operational concepts. The architecture and design of the IT solution is developed along with related documentation.

14 Claims, 18 Drawing Sheets

METHOD AND SYSTEM FOR DEVELOPING A CONCEPTUAL MODEL TO FACILITATE GENERATING A BUSINESS-ALIGNED INFORMATION TECHNOLOGY SOLUTION

FIELD OF THE INVENTION

The present invention relates to a method and system for developing a conceptual model to facilitate generating a business-aligned information technology solution and more particularly to a technique for defining a conceptual structure that includes representations of business-aligned conceptual components and for describing operational concepts based on the conceptual structure to translate business intent into an information technology solution.

BACKGROUND OF THE INVENTION

Conventional techniques for developing information technology (IT) solutions fail to adequately address the need for business stakeholders to understand the organization and structure of IT solutions to facilitate the maintenance of a business-IT alignment (i.e., ensuring that the IT solutions meets overall business intent throughout the life of the IT solution). These known IT solution development techniques are oriented toward specific technologies, applications and versions of software, thereby hindering the capture and active maintenance of an overall solution context for requirements and changes. Other deficiencies and limitations of conventional IT development techniques include making details of the overall business intent unclear to IT development teams, failing to map IT architecture and design rationale back to business intent adequately, not allowing business stakeholders to fully understand how IT solutions are structured and organized in order to make business decisions that minimize required IT solution changes while maximizing business innovation, hindering the engagement of business stakeholders in lifecycle processes for IT solutions and the effective collaboration of business stakeholders with IT stakeholders. Conventional IT development methods include, for example, Structured Design and Programming, Object Oriented Analysis and Design, Component Based Design, Model Driven Architecture, Rational Unified Process, and Service Oriented Modeling and Architecture (SOMA). These examples of conventional IT development methods primarily serve the IT stakeholders, such as IT architects, IT managers and programmers, while impeding a collaborative use of the known development methods that includes business stakeholders. Business stakeholders find the tools and notations used by these known methods to be intimidating and difficult to understand, thereby hindering the business stakeholders from playing a more effective role in architecting IT solutions to meet business needs. Business stakeholders provide input to these known methods, but do not actively participate in the use of these methods. Thus, there exists a need to overcome at least one of the preceding deficiencies and limitations of the related art.

SUMMARY OF THE INVENTION

The present invention provides a method of developing an information technology solution via development of a conceptual model, the method comprising:

defining, by one or more business stakeholders associated with a business, a plurality of requirements of an information technology (IT) solution owned by the business;

developing a conceptual model by the one or more business stakeholders and one or more IT stakeholders associated with the business, the conceptual model providing a representation of a design of the IT solution, the conceptual model including a plurality of conceptual components and a plurality of operational concepts, the plurality of conceptual components representing one or more IT systems, one or more hardware components of the one or more IT systems and one or more software components of the one or more IT systems, and the plurality of operational concepts indicating interactions among the plurality of conceptual components to perform a plurality of functions of the business;

generating, via a computing system, a documentation of the conceptual model, the documentation being available and accessible to the one or more business stakeholders and the one or more IT stakeholders, wherein the generating the documentation of the conceptual model includes documenting the plurality of operational concepts;

developing an architecture and a design of the IT solution by the one or more IT stakeholders; and generating, by the one or more IT stakeholders, a documentation of the architecture and the design of the IT solution.

A system, computer program product, and a process for supporting computing infrastructure that provides at least one support service corresponding to the above-summarized method are also described and claimed herein.

Advantageously, the present invention provides a technique for developing a conceptual model that facilitates the development of IT solutions that are business-aligned throughout the lifecycle of the IT solution. The present invention also significantly improves IT project efficiency, enhances productivity and quality related to IT projects, and produces enormous savings on IT spending by businesses in any type of industry. Further, the conceptual model provided by the present invention promotes a common understanding of IT solutions that facilitates collaboration between business stakeholders and IT stakeholders. Still further, no special training in any IT method is needed to read and understand the operational concepts included in the conceptual model. Common software tools and applications can be used to access and read a description of the operational concepts. Moreover, the conceptual model provides a stable view of an IT solution to all stakeholders regardless of technology decisions and upgrades made to different parts of the IT solution at various times during the lifecycle of the IT solution.

DETAILED DESCRIPTION OF THE INVENTION

1. Overview

The present invention provides a method and system for developing a conceptual model that facilitates the generation of a business-aligned information technology (IT) solution. The conceptual model includes a conceptual structure and operational concepts documentation that are designed to be utilized by both IT stakeholders and business stakeholders. A technology agnostic principle guides the development of the conceptual model in the present invention so that documentation associated with the conceptual model includes descriptions of operational concepts presented at a level of specification that does not include implementation-specific details.

Definitions

The below-listed terms are used herein and are defined as follows:

Information technology solution or IT solution: A collection of IT systems that support activities of a business, where each IT system in the collection is implemented by one or more hardware components and/or one or more software components.

Conceptual model: A high-level abstraction of the design of an IT solution. A conceptual model provides a stable reference for IT solution development and includes a conceptual structure and a description (i.e., documentation) of operational concepts. A conceptual model is owned and understood by both business stakeholders and IT stakeholders.

Conceptual structure: A representation of the basic building blocks of an IT solution. The building blocks represented by the conceptual structure are conceptual components.

Conceptual component: A technology agnostic, modular representation that is one of the building blocks represented by a conceptual structure. A conceptual component is represented as an icon or a form, shape or figure determined by outlines (e.g., a closed plane figure or curve such as a rectangle or circle). When an IT solution is implemented, conceptual components are manifested as software components, hardware components or a combination thereof.

Operational concepts: Descriptions, using a conceptual structure as a basis, of how each conceptual component interacts with one or more other conceptual components to support and perform business functions that an IT solution is meant to support.

Business stakeholders: Non-technical personnel who have an interest in the outcome of an IT solution.

IT stakeholders: Technical personnel who have an interest in the outcome of an IT solution.

2. Conceptual Modeler System

Figure 1:
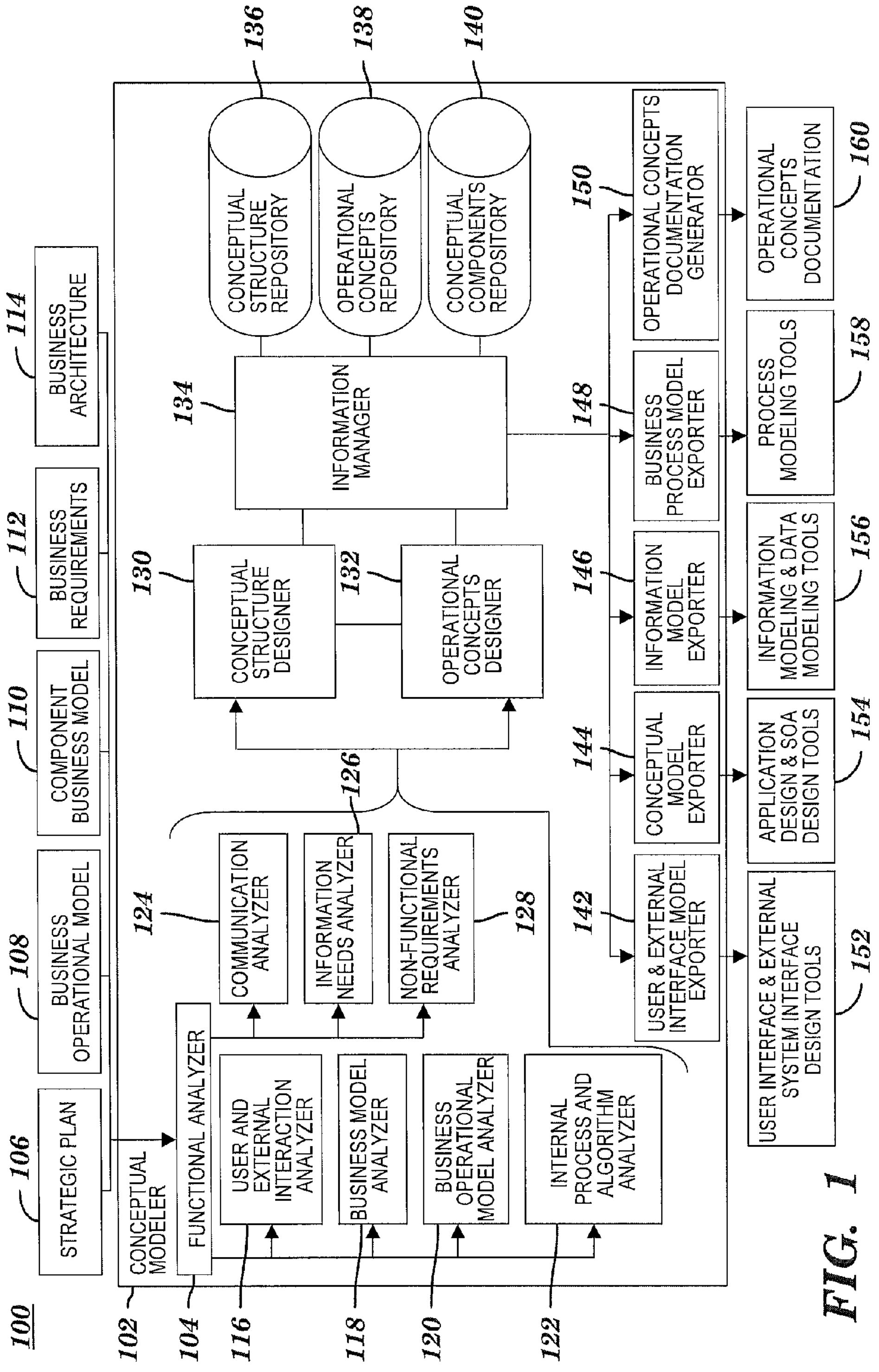
FIG. 1 is a block diagram of a system for developing a conceptual model to facilitate generating a business-aligned information technology solution, in accordance with embodiments of the present invention.

FIG. 1 is a block diagram of a system for developing a conceptual model to facilitate generating a business-aligned IT solution in accordance with embodiments of the present invention. System 100 includes a conceptual modeler 102 that develops a conceptual model to facilitate generating an IT solution that is aligned to a business whose activities are supported by IT solution. Conceptual modeler 102 includes a functional analyzer 104 that analyzes one or more functions of the business (a.k.a. business functions) to support the development of a conceptual structure and a set of operational concepts included in the conceptual model. System 100 also includes the following input from the business domain to functional analyzer 104: a strategic plan 106, a business operational model 108, a component business model 110, one or more business requirements 112 and a business architecture 114. Each of the input items 106-114 are associated with the business whose activities are supported by the IT solution being generated. Strategic plan 106 is provided by, for instance, a strategic planning tool such as an Excel® spreadsheet offered by Microsoft® Corporation of Redmond, Wash. Business operational model 108 is provided by an operational modeling tool that formalizes the interactions between activities of a business. Component business model 110 is provided by a component business modeling tool that implements, for example, the Component Business Model methodology offered by International Business Machines Corporation. Business requirements 112 are provided by a business requirements management tool such as Rational® RequisitePro® offered by International Business Machines Corporation located in Armonk, N.Y. Business architecture 114 is generated by using a combination of diagramming tools such as Microsoft® Visio® and documentation tools such as Microsoft® Word. Process aspects of business architecture 114 are developed, for instance, using Websphere® Business Modeler offered by International Business Machines Corporation. As used herein, business architecture is defined as a view of functional aspects of an IT solution from the perspective of the users, where the functional aspects are derived from an analysis of the existing environment, requirements and constraints of the solution.

Conceptual modeler 102 also includes other analyzers whose analysis activities refine initial versions of the conceptual structure and operational concepts. These other analyzers included in conceptual modeler 102 include a user and external interaction analyzer 116, a business model analyzer 118, a business operational model analyzer 120, an internal process and algorithm analyzer 122, a communication analyzer 124, an information needs analyzer 126 and a non-functional requirements analyzer 128. The functionality of analyzers 104 and 116-128 are described below relative to FIGS. 3 and 4.

Conceptual modeler 102 also includes a conceptual structure designer 130 and an operational concepts designer 132. Conceptual structure designer 130 develops and updates the conceptual structure of the conceptual model being developed by conceptual modeler 102. Operational concepts designer 132 develops and updates the set of operational concepts of the conceptual model being developed by conceptual modeler 102. Input to conceptual structure designer 130 and operational concepts designer 132 include the analysis provided by analyzers 104 and 116-128. Conceptual structure designer 130 iteratively outputs visual representations of the conceptual structure that includes a modular representation of conceptual components. Operational concepts designer 132 iteratively outputs textual descriptions and/or diagrammatic descriptions of the operation of the conceptual components and textual and/or diagrammatic descriptions of how the conceptual components interact with each other. As used herein, textual descriptions refer to verbal descriptions and diagrammatic descriptions include diagrams such as flow charts, sequence diagrams, activity diagrams, etc.

Conceptual modeler 102 also includes an information manager 134, a conceptual structure repository 136, an operational concepts repository 138 and a conceptual components repository 140. Conceptual structure designer 130 stores the conceptual structure and conceptual components in repositories 136 and 140, respectively, by utilizing information manager 134 as an interface. Similarly, operational concepts designer stores the operational concepts in repository 138 by utilizing information manager 134 as an interface. Furthermore, information manager 134 provides operations such as finding, retrieving, capturing, modifying, deleting, and organizing various types of information relevant to the operation of each conceptual component.

In one embodiment, a service oriented architecture is utilized to define the services supported by information manager 134 so that other components such as functional analyzer 104 can invoke the services and access information relevant to the IT solution being developed.

In one embodiment, system 100 is modified so that information manager 134 and repositories 136, 138 and 140 are external to conceptual modeler 102.

Conceptual modeller 102 also includes exporter components 142, 144, 146, 148 and 150 that export information retrieved by information manager 134 to various software tools which are described below. User & external interface model exporter 142 exports to one or more user interface and external system interface design tools 152 information related to how a user and/or other external elements interact with the IT solution being developed. For example, user interface and external system interface design tool 152 includes a tool used to define a storyboard and to design screens for a user interface to the IT solution being developed.

Conceptual model exporter 144 exports modular representations of the conceptual structure to one or more application design and service oriented architecture (SOA) design tools 154. Performing the export of the conceptual structure to design tools 154 ensures that subsequent development of a technical design to implement the IT solution is compliant with the conceptual model throughout the lifecycle of the IT solution.

Information model exporter 146 exports the different types of information required by the IT solution being developed to information modelling & data modelling tools 156, thereby providing a template for information model or data model design. For example, a database that is developed for the IT solution according to the template provided by the export to tools 156 is in compliance with the conceptual model provided by conceptual modeller 102.

Business process model exporter 148 exports to process modeling tools 158 the business processes that are incorporated into the conceptual model. For example, the exported business processes are used as the starting point for process design using Websphere® Business Modeler.

Operational concepts documentation generator 150 exports operational concepts documentation 160. For example, documentation generator 150 causes an operational concepts document 160 to be printed at a printer as a hard copy or electronically transmitted to an authoring software tool.

In one embodiment, the functionalities of all the components of system 100 which are described herein are automated and/or integrated in a software application. In another embodiment, a proper subset of the functionalities of all the components of system 100 which are described herein are automated and/or integrated in a software application.

3. Developing an it Solution

Figure 2:
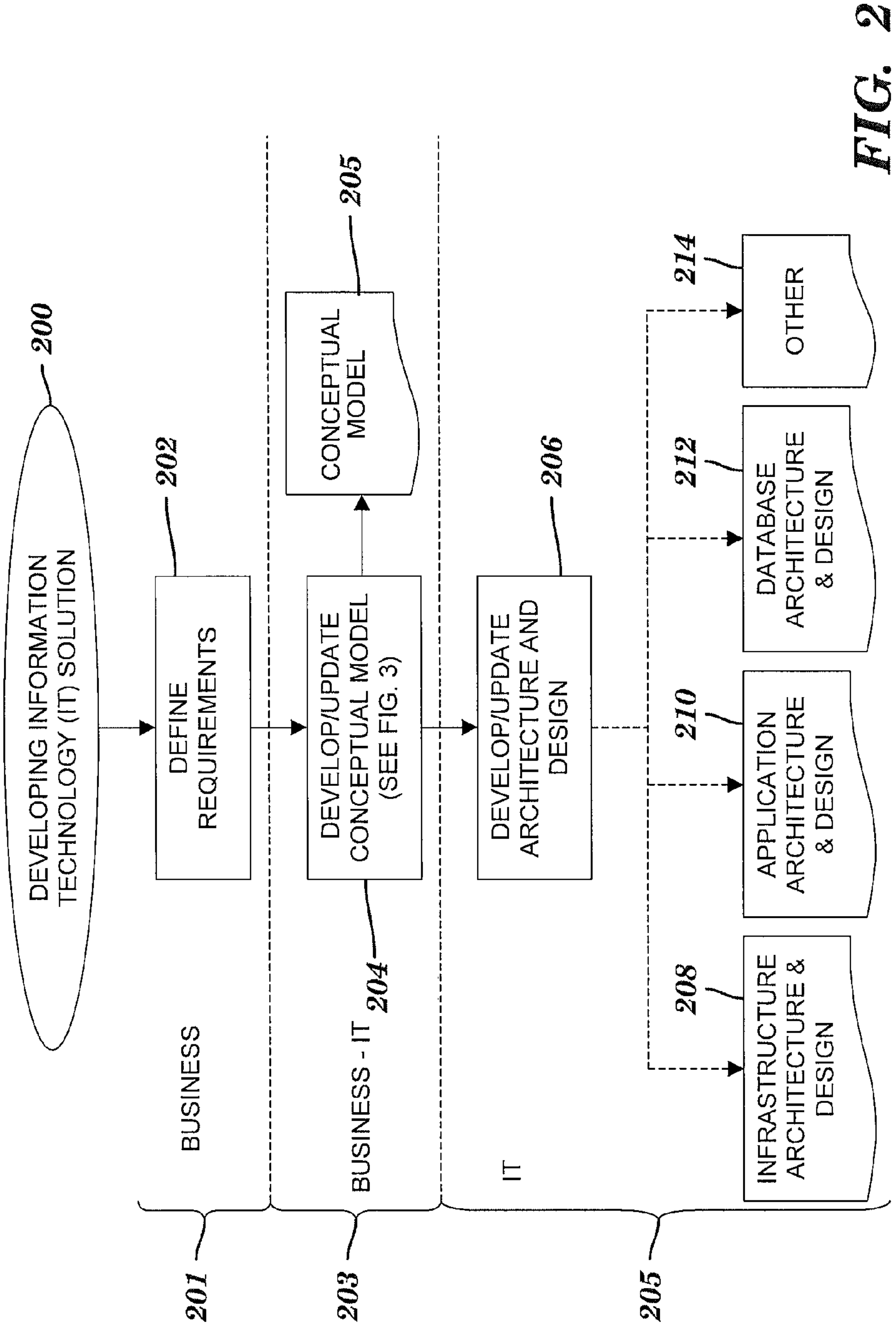
FIG. 2 is a flow diagram of an information technology solution development process implemented by the system of FIG. 1, in accordance with embodiments of the present invention.

FIG. 2 is a flow diagram of an information technology solution development process implemented by the system of FIG. 1, in accordance with embodiments of the present invention. The process of FIG. 2 utilizes development of a conceptual model to serve as a common description of an IT solution that facilitates collaboration between business stakeholders and IT stakeholders, as well as to serve as a high-level abstraction of the design of an IT solution. As used herein, a "common" description of an IT solution is a description that is understood by both business stakeholders and IT stakeholders. As a high-level abstraction of the design of an IT solution, the conceptual model also serves as a stable reference for all IT solution development activities. Being in the common business-IT domain, the conceptual model is owned by both business and IT stakeholders. This joint ownership of the conceptual model by business and IT must be controlled through an appropriate enterprise governance model.

The IT solution development process begins at step 200. In step 202, one or more business stakeholders in a business domain 201 define business requirements related to the IT solution. In step 204, the one or more business stakeholders and one or more IT stakeholders of a business-IT domain 203 develop or update a conceptual model for the IT solution whose requirements are defined in step 202. As used herein, a business-IT domain is defined as a domain of activities whose ownership is shared by both business and IT stakeholders. The output of step 204 is a newly developed or updated conceptual model 205. In step 206, the one or more IT stakeholders of an IT domain 205 develop or update the architecture and design of the IT solution being developed. The output of step 206 includes infrastructure architecture and design 208, application architecture and design 210, database architecture and design 212 and/or other architecture and design 214 associated with the IT solution being developed. Relative to FIG. 2, "architecture" refers to the choice of structure and layout of technical components (i.e., hardware and software) and relationships and interfaces therebetween in order to implement a conceptual model. Also relative to FIG. 2, the term "design" specifies decisions made for an architecture, such as specific vendor products, versions, sizing, and location of hardware and software components, as well as various other details needed to implement software applications and programs and to integrate the software applications and programs with one another and with the hardware components.

4. Developing a Conceptual Model

Figure 3:
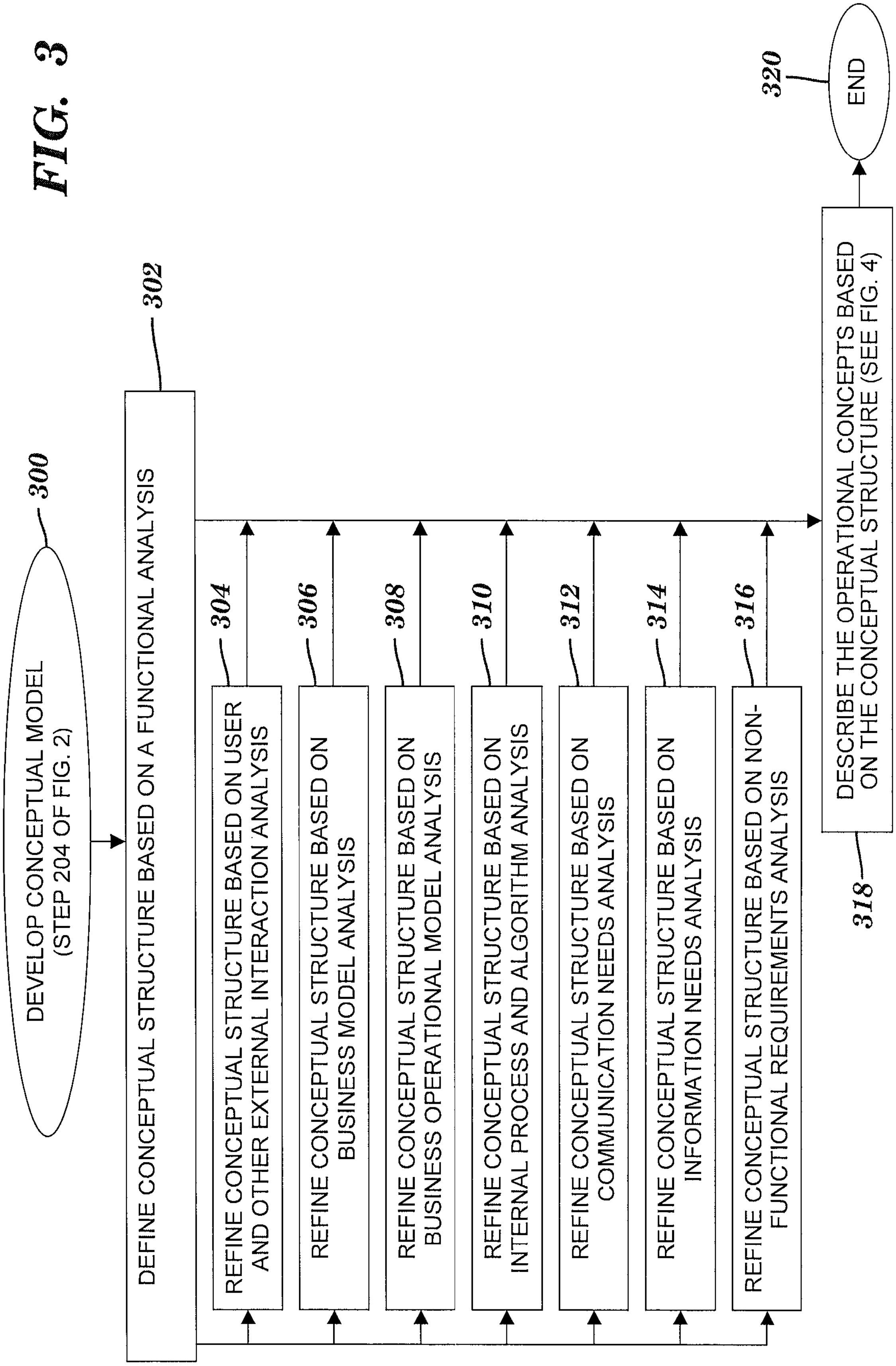
FIG. 3 is a flow diagram of a conceptual model development process included in the process of FIG. 2, in accordance with embodiments of the present invention.

FIG. 3 is a flow diagram of a conceptual model development process included in the process of FIG. 2, in accordance with embodiments of the present invention. Again, a conceptual model consists of a conceptual structure and a description of the operational concepts of an IT solution. The conceptual structure represents the basic building blocks of an IT solution. The building blocks represented by the conceptual structure are technology agnostic, modular representations referred to herein as conceptual components. When an IT solution is implemented, conceptual components are manifested as software components, hardware components or a combination thereof. The operational concepts of an IT solution describe, using the conceptual structure as the basis, how each conceptual component interacts with one or more other conceptual components to support and perform the business functions that the IT solution is meant to support. The conceptual model development process consists of several key activities as shown in FIG. 3.

The conceptual model development process begins at step 300. In step 302, business and IT stakeholders define a conceptual structure based on a functional analysis. In each of steps 304-316, business and IT stakeholders refine the conceptual structure defined in step 302 based on one of the following analyses: a user and other external interaction analysis (see step 304), a business model analysis (see step 306), a business operational model analysis (see step 308), an internal process and algorithm analysis (see step 310), a communication needs analysis (see step 312), an information needs analysis (see step 314), or a non-functional requirements analysis (see step 316). In one embodiment, any combination of steps 304-316 is performed in parallel. In another embodiment, steps 304-316 are performed in any sequence.

When following step 302, step 318 includes generating a description of the operational concepts based on the conceptual structure defined in step 302. When following one of steps 304-316, step 318 includes describing the operational concepts based on the conceptual structure, as refined by the step (i.e., step 304, 306, 308, 310, 312, 314 or 316) that immediately precedes step 318. In one embodiment, the description of the operational concepts is generated manually by business and IT stakeholders in step 318. In another embodiment, the description of the operational concepts is included in documentation that is generated automatically in a pre-defined format in step 318 by using the conceptual structure and the results of the analyses in steps 302-316 as input. Any aspect of automatically generated operational concept documentation can be overridden and modified via manual controls. The conceptual model development process ends at step 320.

Steps 302-318 are described in more detail below.

Functional analysis (step 302): The functional analysis of step 302 includes an analysis of the business functions to be supported by the IT solution. This analysis of business functions reveals an initial, basic set of conceptual components that are needed in the IT solution. The goal at this initial stage of conceptual component identification is to be comprehensive in the coverage of the needed functions. Other considerations such as how the conceptual components are aggregated or partitioned to optimize and accommodate various other business and technical requirements are addressed by steps 304-316. The collection of conceptual components identified at step 302 represents an IT solution (hereinafter, also referred to as "the solution"). The operational concepts description of step 318 is started during and/or after the functional analysis of step 302.

User and other external interaction analysis (step 304): Analysis of the interactions that one or more users and other elements external to the solution (i.e., the solution identified by step 302) are to have with the solution determines whether additional systems (a.k.a. IT systems), subsystems, and/or conceptual components are needed in the solution. If step 304 determines a need for such conceptual components systems and/or subsystems, then step 304 also identifies the specific conceptual components systems and/or subsystems that are to be added. The one or more added systems or subsystems are, for example, partitioned into conceptual components needed to support the systems' or subsystems' functions and operations. In step 304, the conceptual components in the systems and subsystems are identified based on a need to support the external interactions that the solution must have. For example, Web 2.0 and Enterprise 2.0 are tag names that are used to refer to a variety of interactions and collaborations enabled by emerging technologies. These emerging technologies include instant messaging, collaborative content tools, integrated search tools, unified communications, wikis, mashups, RSS feeds, blogs among employees, partners or customers, presence awareness, business social networks, and click-to-call communication. During and/or after step 304, the operational concepts description is updated in step 318 to capture the changes made to the conceptual structure and descriptions of the aforementioned analyzed interactions.

Business model analysis (step 306): The conceptual structure of the IT solution must align with the business model for the client (i.e., the business) who will own and use the IT solution (hereinafter referred to as "the client"). In step 306, the implications of the client's business model to the conceptual structure are examined and the conceptual structure is updated accordingly. Considerations in step 306 include software or system licensing models, software or system usage fee structures, technology development joint ventures, monitoring and tracking requirements to meet regulatory and other business policy mandates, and governance requirements. These considerations must be applied to the solution and all of its systems and subsystems. As a result of the analysis of step 306, new conceptual components are added and/or existing conceptual components are modified by partitioning or aggregating the conceptual components. In some cases, new systems, subsystems and conceptual components that were not apparent in the earlier analyses are identified at step 306.

Business operational model analysis (step 308): The conceptual structure of the IT solution being developed must enable and support the execution of the business operational model for the client. Given the conceptual components of the IT solution, the analysis of step 308 determines how these conceptual components need to interact with each other in order to support the business operational model. As used herein, a business operational model is defined as a description, by business stakeholders, of how a business operates to meet business operational goals. While automating business operations, IT solutions must preserve and enable the operational behaviors intended by the business. Design constraints in an IT solution must not require the business to behave in unintended ways. The analysis of step 308 includes describing how the different conceptual components in the solution interact with each other to perform the business functions and confirming that these interactions are consistent with the business operational model. In one embodiment, aggregation and/or partitioning of conceptual components to enable required interactions among conceptual components results from the analysis of step 308. In some cases, new conceptual components are identified to allow certain interactions to be described at a more detailed level. During the analysis of step 308, the operational concepts description is updated to capture the descriptions of the aforementioned interactions among the conceptual components, the IT solution and its systems and subsystems, and external entities including users.

Internal process and algorithm analysis (step 310): At the time of initiating step 310, most conceptual components that make up the IT solution and its systems and subsystems have been identified. The operational concepts description provided by step 318 includes descriptions of these conceptual components and how the conceptual components interact to perform pre-specified business functions. As the operational concepts are developed in detail by step 318, attention is drawn to the internal processes and algorithms of the IT solution that require detailed analysis of the operation of specific conceptual components and their interactions. As used herein, an internal process is a method by which computing structures (e.g., data structures) and algorithms internal to a conceptual component are utilized to perform a required function. In one embodiment, such analysis in step 310 leads to further partitioning of conceptual components and/or aggregation of conceptual components. In some cases, new conceptual components need to be defined to enable the description of specific internal processes or the business logic behind specific algorithms. The internal processes and the algorithms developed in step 310 are captured within the operational concepts description of step 318.

Communication needs analysis (step 312): The conceptual structure defined up to step 312 consists of conceptual components that were identified through a variety of analyses. Such analyses included examining functional requirements (see step 302), external interactions such as with users and external systems (see step 304), a business model (see step 306), a business operational model (see step 308), and internal processes and algorithms (see step 310). Communication requirements among the various conceptual components, among the solution and its one or more systems and one or more subsystems, as well as among the solution and various systems external to the solution are examined closely in step 312. The examination of communication requirements in step 312 identifies conceptual components and subcomponents that are to be added to the system to support a variety of communication needs, including filesharing, file transfer, web services, web browser, and other Internet, intranet, and local area network communications. The intent of step 312 is to identify new communication-specific conceptual components and subcomponents needed to support the required communication capabilities in the system. In step 318 that follows step 312, the operational concepts description is extended to include the operation of the different communication-specific conceptual components and subcomponents identified in step 312, as well as the interactions of the identified communication-specific conceptual components and subcomponents with the rest of the solution, the one or more systems, the one or more subsystems and external systems.

Information needs analysis (step 314): As the conceptual structure and the corresponding operational concepts are developed (e.g., developed via steps 302-312 and 318), a variety of information needs to support the operational concepts emerges. The information needs are captured and represented in the conceptual model through descriptions of information manager 134 (see FIG. 1) and information repository components 136, 138 and 140 (see FIG. 1). Information manager 134 (see FIG. 1) is a conceptual component that captures, stores, retrieves and manages all information internal to the system. Information repositories 136, 138 and 140 (see FIG. 1) represent the conceptual storage repositories for different types of information within the scope of information manager 134 (see FIG. 1). In one embodiment, a system or subsystem also has its own information manager and information repositories, if needed.

Description of information manager 134 (see FIG. 1) within the operational concepts description resulting from step 318 identifies the conceptual information-related functions (a.k.a. operations) that information manager 134 (see FIG. 1) supports, including finding, retrieving, capturing, modifying, deleting, and organizing various types of information relevant to the solution. In addition, information manager 134 (see FIG. 1) itself is partitioned into conceptual components that together enable the information manager to perform the various conceptual information-related functions. The operation of information manager 134 (see FIG. 1) is described in the operational concepts description in terms of the interactions among the information manager's components.

In one embodiment, the system and the system's one or more subsystems have one or more information repositories depending upon the need to model the information repositories at a conceptual level at an adequate level of detail while not overly complicating the description of the operational concepts.

Non-functional requirements analysis (step 316): Non-functional requirements specify additional quality constraints that a solution must meet in addition to the requirements described above relative to steps 302-314. Non-functional requirements include, for example, one or more of the following considerations:

Availability: Requirements related to how the solution stays accessible to end users as pre-specified in spite of potential system and component failures.

Backup & Recovery: Requirements related to how information on solution functions are stored at various points during normal operation and how such stored information is used to restore normal operation following system and component failures.

Capacity Estimates and Planning: The ability of the solution to accommodate planned and unplanned increases in the usage load on the solution.

Configuration Management: Requirements related to how the solution can be customized and adapted to meet specialized needs of the business and users.

Disaster Recovery: Special operational procedures required for the operational continuity of the solution in the event of disasters such as tornadoes and floods.

Extensibility/Flexibility: Special considerations required to add new business functions to the solution or support new technologies.

Failure Management: Requirements related to how the solution handles hardware, software, and network failures.

Performance: The solution response time requirements to meet business needs,

Reliability: The ability of the solution to support functionality in a predictable and reliable manner.

Scalability: The ability to expand the solution to accommodate more users, more transactions and more data as additional users and data are added in the future.

Security: Various commonly known security requirements such as access control, authentication/identification, confidentiality, integrity, accountability, administration/configuration, and assurance/monitoring.

Service Level Agreements: Business contractual agreements between users of the solution and the operator of the solution regarding operational goals for the system.

System Management: Capabilities in the solution to ensure the continued monitoring of the solution to ensure that acceptable availability is maintained and to allow the updates to the solution infrastructure to occur in an orderly manner.

Quality of Service: The ability of the solution to detect and compensate for potential overload situations.

In step 316, the conceptual structure is examined closely from the perspective of the non-functional requirements of the solution. The analysis of step 316 identifies whether there is a need for new conceptual components and/or determines whether partitioning and/or aggregation of already identified conceptual components is needed in order to enable the solution and the solution's systems and subsystems to meet the non-functional requirements. The non-functional requirements considered and the operational implications to impacted conceptual components are described in the operational concepts description that results from step 318 that follows step 316. Thus, steps 316 and 318 ensure that the conceptual structure of the solution is adequately detailed to be able to describe the concepts behind how the non-functional requirements are satisfied by the solution.

Describing the operational concepts based on the conceptual structure (step 318): The description of the operational concepts resulting from step 318 describes an IT solution and how the IT solution serves the needs of a business. This description of the operational concepts is understood by both business stakeholders and IT stakeholders of the IT solution. This understanding shared by both business and IT stakeholders enables a continuous alignment between the business domain and the IT domain, regardless of changes in technologies, applications, and software products that constitute the IT solution. The operational concepts description provided by step 318 is technology agnostic and provides a stable view of an IT solution that is only modified through governance processes jointly owned by business and IT stakeholders. The operational concepts are captured in sufficient detail in step 318, but not any more than that, in order to improve the clarity, to both business and IT stakeholders, regarding how the IT solution serves the business needs by describing the various components of the IT solution at a conceptual level, how the components interact with one another, and the components' internal processes and algorithms. The operational concepts description provides an end-to-end view of the IT solution, including all of the IT solution's systems and subsystems. Thus, the operational concepts description is a stable reference to the IT solution that facilitates the making of more informed business decisions by business stakeholders that minimize changes to IT solution while leveraging the IT solution for maximum business innovation. The operational concepts description is also useful to IT stakeholders by being a stable reference to the IT solution that provides an end-to-end view of the solution and that explains how the different components of the IT solution together support the business. The process of developing the operational concepts description and how this description is organized is described below relative to FIG. 4.

As used herein, a description "at a conceptual level" (e.g., "describing the various components of the IT solution at a conceptual level" as presented above) is defined as a description based on conceptual components and is therefore a high-level or abstract-level description and not a low-level or concrete-level description of an actual implementation of an IT solution. The description at a conceptual level (i.e., the high-level description based on conceptual components) is also called a conceptual description of an IT solution. Any implementation of the conceptual description of the IT solution is an instantiation of the solution. When an IT solution is implemented in compliance with the conceptual model of the IT solution, the structure and operational behavior of every instance of the IT solution can be validated against the conceptual structure and the operational concepts provided by the conceptual model, regardless of variations in the choice of technologies, applications, and software products to implement the IT solution or any part thereof.

As used herein, an instance of the IT solution is validated against the conceptual structure and operational concepts provided by a conceptual model if the following criteria are satisfied:

1. the structural elements of the instance of the IT solution can be mapped readily to conceptual components in the conceptual structure, even though the mapping does not have to be one-to-one mapping;

2. the structural elements of the instance of the IT solution, from the viewpoint of the conceptual components, behave as described in the operational concepts;

3. functions (or services) implemented in the instance of the IT solution can be mapped readily to the functions described by the operational concepts; and 4. functions (or services) implemented in the instance of the IT solution, from the viewpoint of the functions described in the operational concepts, behave as described by the operational concepts.

5. Describing Operational Concepts

Figure 4:
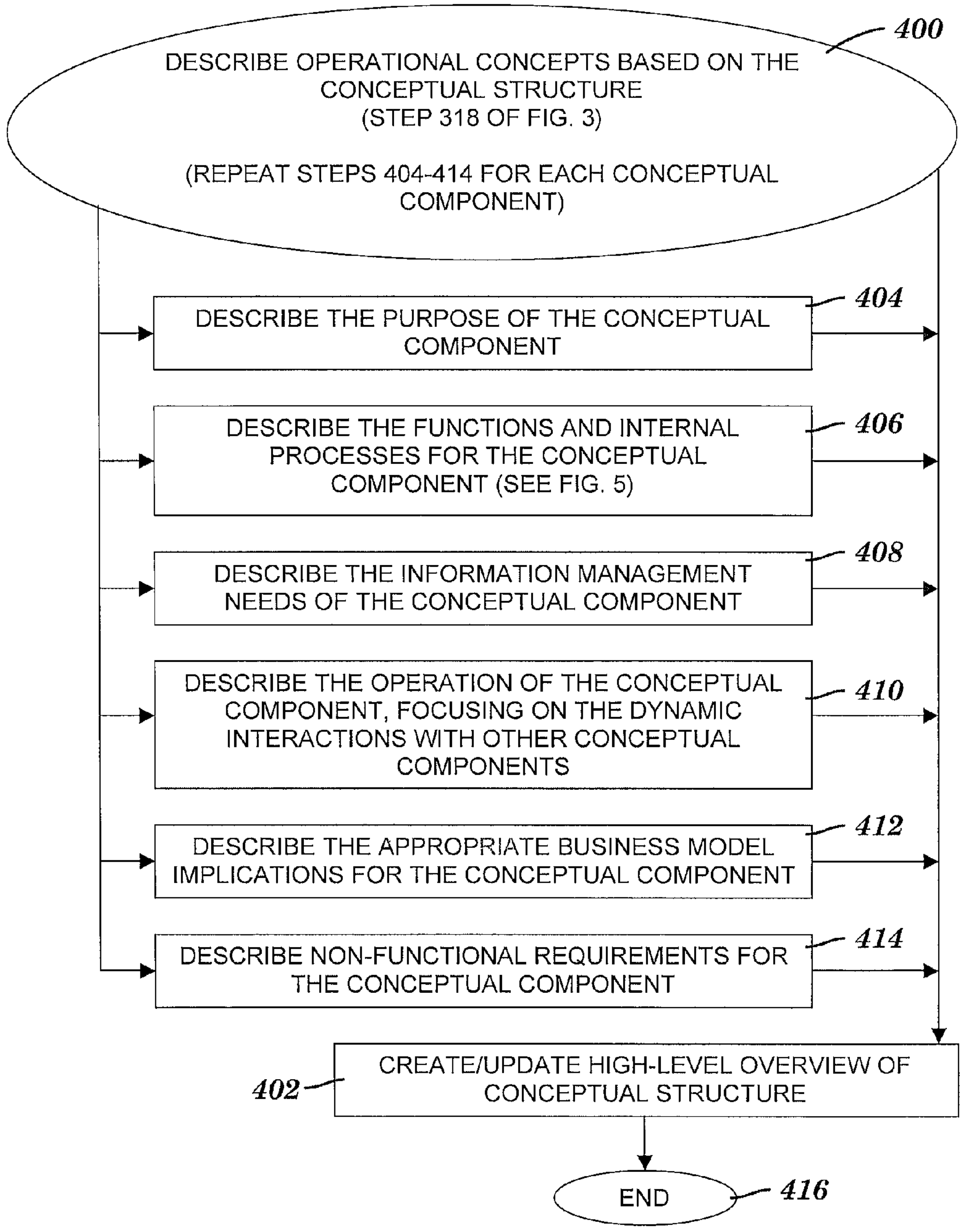
FIG. 4 is a flow diagram of an operational concepts description process included in the process of FIG. 3, in accordance with embodiments of the present invention.

FIG. 4 is a flow diagram of an operational concepts description process included in step 318 of FIG. 3, in accordance with embodiments of the present invention. The development of the operational concepts description is an iterative process that begins when an initial set of conceptual components is identified as described in step 302 of FIG. 3. The process of FIG. 4 provides an end-to-end overview of the solution, as well as detailed descriptions of the different conceptual components, the functions they support, their internal processes and algorithms, and their information management needs. Furthermore, the process of FIG. 4 provides a description of how conceptual components interact with one another in supporting the business functions and the implications of the client's business model to the organization of the conceptual components, including the way the conceptual components are partitioned and aggregated. Finally, the process of FIG. 4 also provides a description of how different non-functional requirements, such as integration, reliability, performance, and maintenance, are handled at the solution level as well as at the component level. The steps of the operational concepts description process of FIG. 4 are described below in more detail.

The process of describing operational concepts starts at step 400. In an initial performance of step 402 which immediately follows step 400, the business and IT stakeholders create a high-level overview of the conceptual structure to develop an end-to-end view of the solution. Step 402 is also iteratively performed as a follow-up step to any of steps 404-414 for the conceptual component currently being processed or for a subsequent conceptual component. When step 402 is performed as a follow-up to step 404, 406, 408, 410, 412 or 414, the business and IT stakeholders update the high-level overview of the conceptual structure that is created in the initial performance of step 402. The update of the high-level overview generated by step 402 is based on one of the specific descriptions provided by the step that immediately precedes step 402 (i.e., one of steps 404-414). These specific descriptions are described below relative to steps 404-414. In one embodiment, any combination of steps 404-414 is performed in parallel. In another embodiment, steps 404-414 are performed in any sequence.

For large and complex solutions, it may be necessary to aggregate the conceptual components into fewer top-level conceptual components in order to be able to produce a simplified end-to-end view of the solution that reduces clutter. The overview provided by step 402 is comprehensive and accurate, but is not detailed.

The high-level overview of step 402 must consist of at least one overall (a.k.a. overview) diagram that shows the end-to-end solution. Significant systems and significant subsystems in the solution are identified at this overall diagram level as needed to provide a high-level description of the conceptual structure and the operational concepts, while avoiding the detail and clutter of low-level descriptions, where the aforementioned description of the conceptual structure is characterized as high-level rather than low-level based on pre-defined criteria. As many additional diagrams as are needed are added to provide further drill-down details of the solution, systems, sub-systems, and components.

Operation of the solution is described using the overall diagram as well as the more detailed drill-down diagrams. The operational descriptions help business and IT stakeholders to understand the business goals for the IT solution and how the IT solution and its systems and subsystems together operate to deliver on the business goals.

Any number of illustrative techniques are used to communicate important concepts in step 402. Such techniques include, for example, sequence diagrams, component interaction diagrams, state diagrams, and collaboration diagrams. In one embodiment, usage of standard IT conventions is avoided in order to make the operational concepts description non-threatening to non-technical business stakeholders. However, the exact notations and conventions that are acceptable depend on the degree of familiarity among the business and IT stakeholder community that use the documentation resulting from step 402.

Non-functional requirements that are significant at the system level are described in the high-level overview created or updated in step 402.

Again, the high-level overview is developed iteratively. As the activities described below relative to steps 404-414 are completed for each conceptual component, the high-level overview evolves toward final completion via updates performed in repeated applications of step 402.

Steps 402 through 414, inclusive, are performed by business and IT stakeholders and are repeated for each conceptual component in the conceptual structure.

In step 404, the business purpose of a conceptual component is documented in the operational concepts description. Step 404 describes the unique value of the conceptual component to the solution, system or subsystem and how the conceptual component is used with regard to the overall operation of the solution.

In step 406, the functions and internal processes for the conceptual component are identified, described and included in the operational concepts description. The activity in step 406 closely examines the functions of a conceptual component. Major functions that are supported by a conceptual component are identified and described in detail, although at a conceptual level only. Functions identified and described in step 406 include those functions needed to enable conceptual component-level interactions. A conceptual component-level interaction is an interaction between a conceptual component and another conceptual component. Conceptual component-level interactions occur only through the functions intended for such interactions and supported by the respective conceptual components. The activity of step 406 is described in more detail below relative to FIG. 5.

In step 408, the information management needs of the conceptual component are described and included in the operational concepts description. All information-related functions that must be supported through information manager 134 (see FIG. 1), including finding, retrieving, capturing, modifying, deleting, and organizing various types of information relevant to the operation of the conceptual component are identified in step 408. Each identified information-related function is described in step 408, including the function's purpose, inputs, and outputs. The descriptions of the information-related functions are at a conceptual level only and are technology agnostic. In one embodiment, the information-related functions identified in step 408 are implemented as services defined by SOA tools and methods.

In step 410, the operation of the conceptual component is described and included in the operational concepts description, focusing on the dynamic interactions between the conceptual component and other conceptual components. The activity of step 410 involves describing the interactions that a conceptual component has with the rest of the solution and the solution's systems, subsystems and components in performing the conceptual component's functions. The interactions are observed from the point-of-view of the conceptual component and described as such. As described above relative to step 406, conceptual component-level interactions occur only through the functions intended for such interactions and supported by the respective conceptual components. Thus, when complete, the description provided by step 410 provides a holistic view of all the interactions of the conceptual component with regard to the solution.

In step 412, the appropriate business model implications for the conceptual component are described and included in the operational concepts description. Prior to step 412, conceptual components were identified through several types of analyses as described in steps 302-316 of FIG. 3. Step 306 of FIG. 3 involves examining the conceptual structure of the system for alignment with the client's business model. The different considerations described for step 306 of FIG. 3 may impact the solution, its one or more systems, its one or more subsystems and/or its components. Any of the impacts resulting from step 306 (see FIG. 3) that affect the conceptual component currently being examined are documented in step 412.

In step 414, the non-functional requirements for the conceptual component are described and included in the operational concepts description. Different non-functional requirements that are significant at the level of the conceptual component being examined are described through the activity of step 414. The non-functional requirements analysis was described above relative to step 316 (see FIG. 3).

6. Describing Functions and Internal Processes

Figure 5:
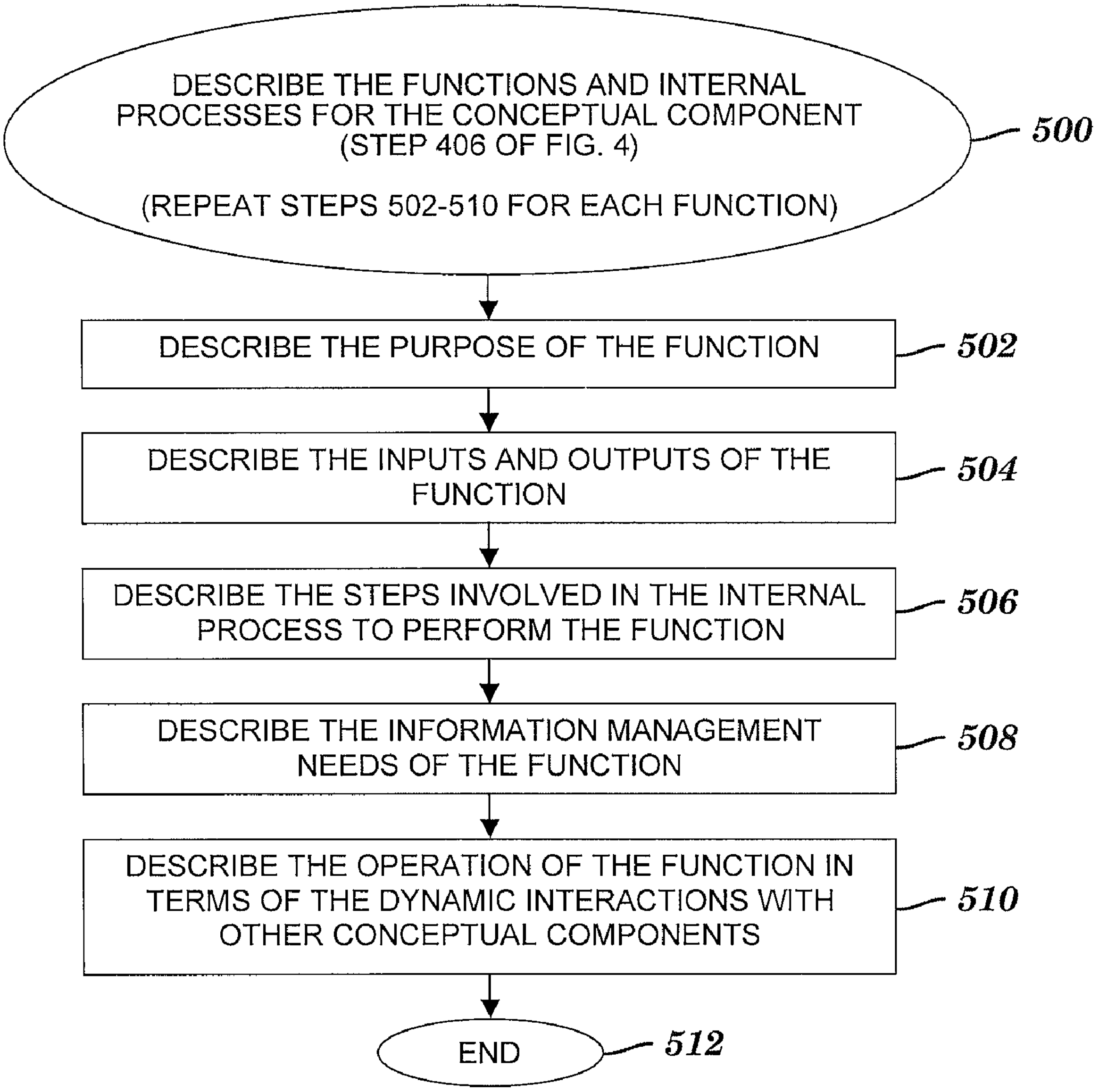
FIG. 5 is a flow diagram of a process that describes the functions and internal processes for a conceptual component, and that is included in the process of FIG. 4, in accordance with embodiments of the present invention.

FIG. 5 is a flow diagram of a process that describes the functions and internal processes for a conceptual component, and that is included in the process of FIG. 4, in accordance with embodiments of the present invention. The process of FIG. 5 provides the details for step 406 of FIG. 4. The process of describing the functions and internal processes for a conceptual component begins at step 500. Steps 502-510 are performed by the business and IT stakeholders and are repeated for each function associated with the conceptual component. In one embodiment, the functions described in the process of FIG. 5 are implemented as services defined by SOA tools and methods. The functions described in the process of FIG. 5 are implemented using the same technologies or different (i.e., hybrid) technologies. As an example of using hybrid technologies, some of the functions in a conceptual model are implemented as services, while other functions of the same conceptual model are implemented using client-server, code library calls such as Dynamic Link Library (DLL) and subroutine calls, etc. Thus, the present invention allows an IT solution implemented with hybrid technologies to be compliant with the conceptual model. One of the significant benefits of the conceptual model is that it offers a stable view of the IT solution to both business and IT stakeholders regardless of various technology decisions and upgrades made at different times to different parts of the IT solution during the lifecycle of the IT solution.

In step 502, the business purpose of a function associated with the conceptual component is described. The unique value that the function adds to the conceptual component is also documented in step 502. Given that the activity of step 502 is nested within step 318 (see FIG. 3), which describes the operational concepts of the conceptual component, the focus of step 502 is on articulating clearly how the function contributes toward supporting the operations of the conceptual component to which the function belongs.

In step 504, the inputs and outputs of the function are described. The different input and output information related to the function is documented at a conceptual level in step 504. The focus of the step 504 activity is on clarifying how the function can be invoked to obtain pre-defined business value from the function.

In step 506, the steps involved in the internal process that performs the function is described. Step 506 provides a conceptual description of the algorithms and internal process steps that perform the function. The steps involved in executing the function are described at a conceptual level. Significant computing structures internal to the conceptual component that play a key role in the operation of the function are referenced appropriately in the description provided by step 506. The activity of step 506 constrains implementation designs for the function as needed to maintain stability of the operation and behavior of the function, but only to the extent that is essential to meet the business objectives, by describing in adequate detail how the function is expected to operate by relying on computing structures and processes internal to the conceptual component. The aforementioned conceptual description of the algorithms and internal process steps that perform the function provides a stable view of the function, the function's operation, and the function's relationships to key computing structures, regardless of specific technology and design details that can vary from one implementation of the function to another.

In step 508, the information management needs of the function are described. All information-related functions that must be supported through information manager 134 (see FIG. 1), including finding, retrieving, capturing, modifying, deleting, and organizing various types of information relevant to the operation of the function are identified in step 508. Each information-related function is described in step 508, including its purpose, inputs, and outputs. The descriptions of the information-related functions are at a conceptual level only and are technology agnostic. The information-related functions described in step 508 are implemented using the same technologies or hybrid technologies.

In step 510, the operation of the function in terms of the dynamic interactions with other conceptual components is described. The interactions with other conceptual components that are needed for the proper operation of the function are described in the activity of step 510. Step 506 describes how the function relies on computing structures within the conceptual component. The focus of the activity of step 510 is on higher-level interactions, namely, conceptual component-level interactions involved in the operation of the function. Descriptions of conceptual component-level interactions may refer to functions supported by other conceptual components, as well as to computing structures within those other conceptual components. However, conceptual component-level interactions occur only through the functions intended for such interactions and supported by the respective conceptual components. The aforementioned conceptual description of the algorithms and internal process steps that perform the function provides a stable view of the function, the function's operation, and the function's relationships to other conceptual components, regardless of specific technology and design details that can vary for conceptual components from one implementation to another.

7. Learning Solution Example

In the example (a.k.a. the learning solution example) provided in this section, there is a need to build an online learning solution for a client. The requirements of the online learning solution are expressed in six categories as described below:

Functional:

1. The online learning solution is a web-based solution that allows anytime, anywhere access to anyone on the Internet to online multimedia learning content.
2. The learning content can be accessed as complete courses or as individual modules of the course.
3. Instructors can register students into the learning solution.
4. Instructors can browse through any course or module.
5. Instructors can assign courses or modules for students.
6. Instructors can view or generate a report listing all students enrolled in a course or module.
7. Students can view a listing of all the courses modules in which they are enrolled and access the learning content.
8. Historical information on the content accessed by each student and their completion status is retained in the learning solution.

9. Students can access historical information on learning material they have completed and access any of the corresponding learning material.
10. Instructors can add any browser-compatible course content into the learning solution.
11. Instructors can author content on their own and add the content into the learning solution.
12. Instructors can search for and browse through appropriate learning content.

Access and Security:

1. Students will have access only to the courses and modules assigned to them by instructors.
2. Only authorized instructors and authorized students can access the learning solution.

End User Access Methods:

1. Instructors and students can access the learning solution over the Internet using web browsers.
2. Students can access content through a variety of end-user devices including desktops, laptops, personal digital assistants (PDAs), and mobile phones; learning content must be delivered in a manner appropriate to the end user device.

Internal Processing Requirements:

1. Content added into the learning solution must be checked for suitability of the content for delivery to the different end user devices. If needed, the content is reformatted as needed to enable such delivery. Content in formats incompatible with the end user devices must be rejected.

Development Plan:

1. The client wants to develop the learning solution over three phases, incrementally adding additional functionality to the learning solution each time.
2. The client wants to defer the learning content search capability until Phase 2.
3. The client wants to defer the capability to access content from partner learning systems until Phase 3.

Business Model and Strategy:

1. A content access fee is payable to third-party vendors each time a third-party learning content in the learning solution is accessed by a student.
2. Instructor-authored content is free for company employees.
3. In the future, the client may want to partner with other learning solution providers and enable access to content available on third-party learning systems or catalogs over the Internet.

Non-Functional Requirements:

1. The system must be customizable to support private-labelled versions of the learning solution. Private-labelling involves customizing the look-and-feel of the user-interface to a limited extent, including changing color schemes, logos, fonts, etc. The client would like this capability in order to have the option of marketing the system as a licensed product to customers.

The remaining portions of the learning solution example section develop a conceptual model for the learning solution example using the steps described above relative to FIG. 3.

7.1 Functional Analysis

Step 302 (see FIG. 3) identifies the major functional capabilities needed in the learning solution. As one example, a business requirements specification is a main source of input for the activity of step 302 (see FIG. 3). The need for functional capabilities can also be identified through an analysis of other sources, such as business strategy descriptions (e.g., strategic plans, Component Business Model, and operational models for an enterprise).

Figure 6:
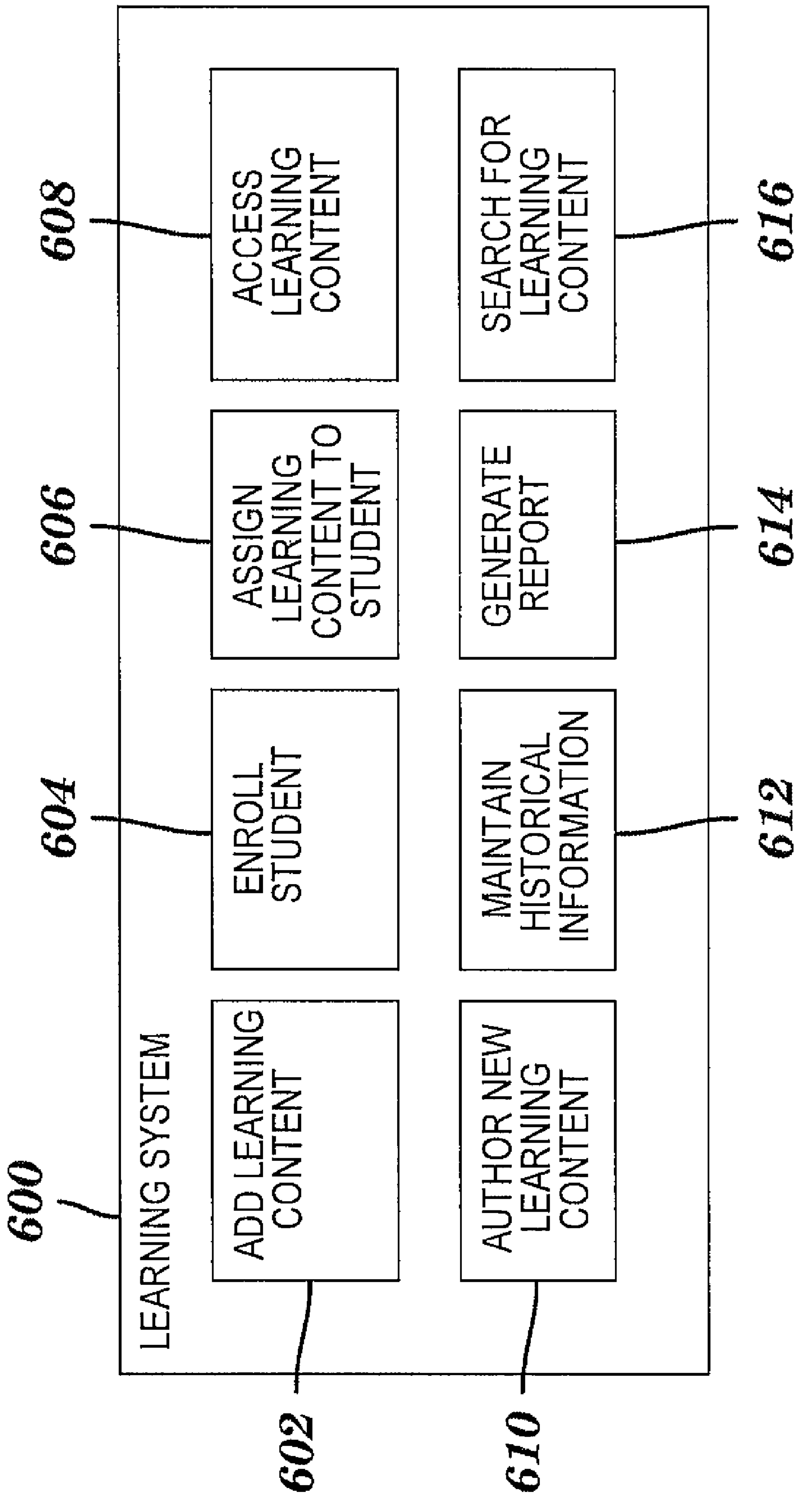
FIG. 6 is an exemplary conceptual structure based on a functional analysis included in the process of FIG. 3, in accordance with embodiments of the present invention.

FIG. 6 is an exemplary conceptual structure based on a functional analysis included step 302 of FIG. 3, in accordance with embodiments of the present invention. FIG. 6 depicts an initial version of a conceptual structure that is based on the learning solution requirements specified above. The learning solution conceptual structure includes learning system 600 and the following conceptual components included in system 600: add learning content 602, enroll student 604, assign learning content to student 606, access learning content 608, author new learning content 610, maintain historical information 612, generate report 614 and search for learning content 616.

7.2 User and Other External Interaction Analysis

Figure 7:
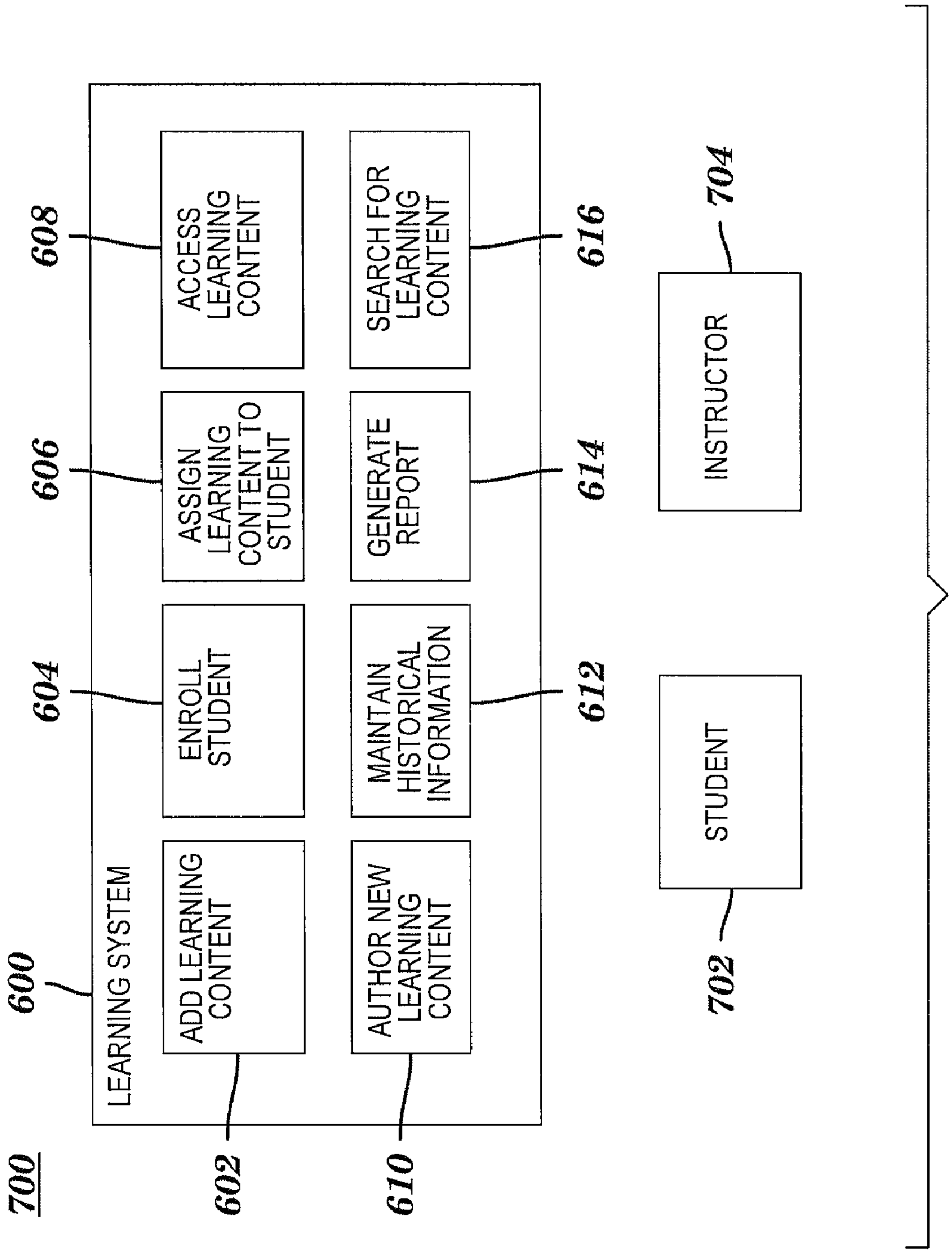
FIG. 7 is a conceptual structure generated by modifying the conceptual structure of FIG. 6 via a user and other external interaction analysis included in the process of FIG. 3, in accordance with embodiments of the present invention.

FIG. 7 is a conceptual structure 700 generated by modifying the conceptual structure of FIG. 6 via a user and other external interaction analysis included in step 304 of FIG. 3, in accordance with embodiments of the present invention. As applied to the learning solution example, step 304 (see FIG. 3) analyzes the different users identified and their interactions with learning system 600. Sources for the step 304 (see FIG. 3) analysis include, for example, the operational model and business requirements, including use cases, if available. Based on an analysis of user interactions from the descriptions of the learning solution requirements listed above, the conceptual structure of FIG. 6 is refined as shown in FIG. 7. Conceptual structure 700 retains learning system 600 and the aforementioned conceptual components 602-616 (see also FIG. 6) and also includes a student system 702 and an instructor system 704, which are two conceptual systems that have been added to represent users—student and instructor, respectively—in conceptual structure 700.

7.3 Business Model Analysis

Figure 8:
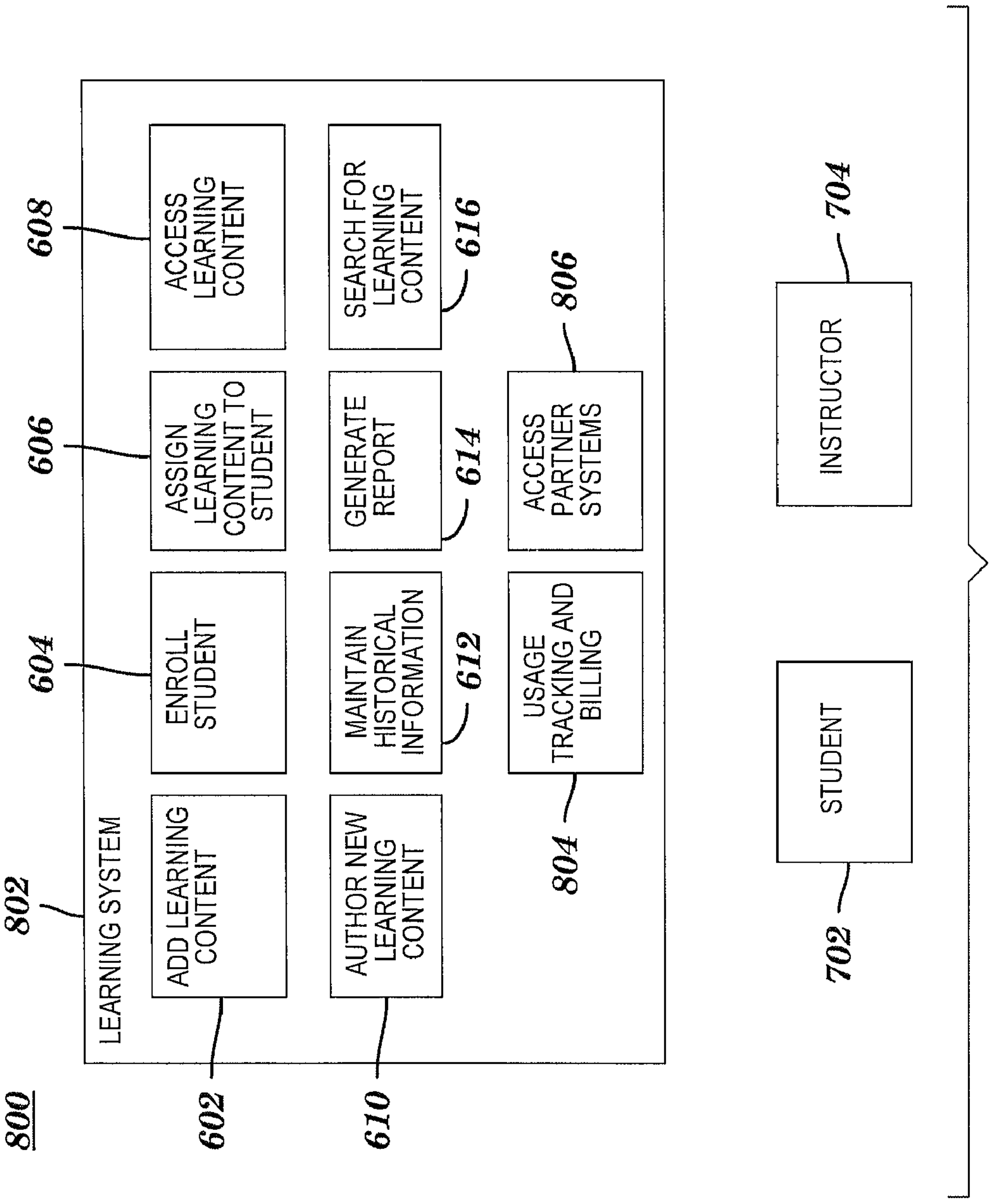
FIG. 8 is a conceptual structure generated by modifying the conceptual structure of FIG. 7 via a business model analysis included in the process of FIG. 3, in accordance with embodiments of the present invention.

FIG. 8 is a conceptual structure 800 generated by modifying the conceptual structure of FIG. 7 via a business model analysis included in step 306 of FIG. 3, in accordance with embodiments of the present invention. As applied to the learning solution example, step 306 (see FIG. 3) examines the implications of the client's pre-specified business model to conceptual structure 700 (see FIG. 7) and updates the conceptual structure accordingly. The updated conceptual structure 800 in FIG. 8 includes an updated learning system 802 that includes the same conceptual components 602-616 and systems 702 and 704 as shown in FIG. 7, but also includes two newly added conceptual components: usage tracking and billing 804 and access partner systems 806. The requirements defined under the "Business Model and Strategy" category listed above indicate that usage tracking and billing 804 and access partner systems 806 must be added to learning system 802.

7.4 Business Operational Model Analysis

Figure 9:
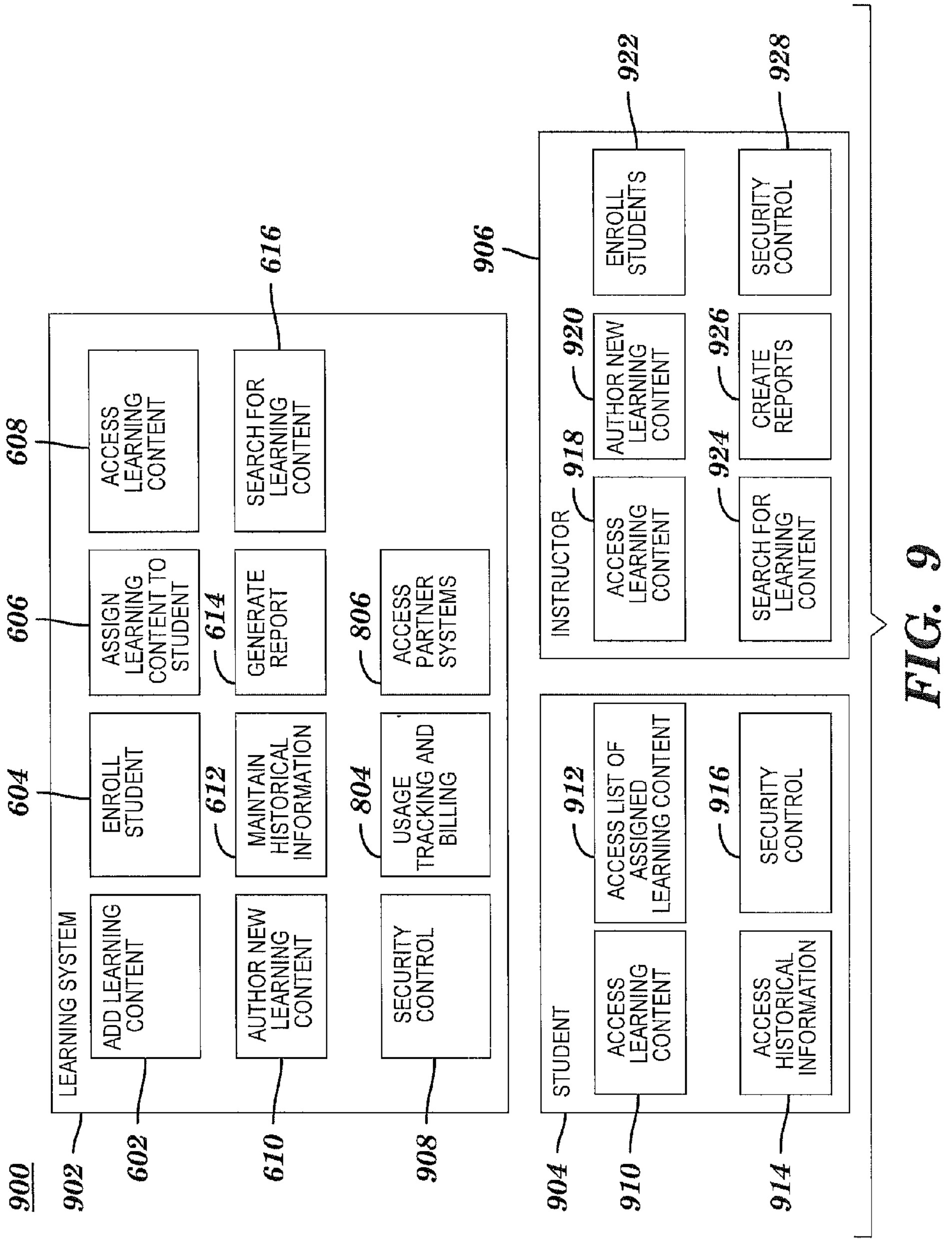
FIG. 9 is a conceptual structure generated by modifying the conceptual structure of FIG. 8 via a business operational model analysis included in the process of FIG. 3, in accordance with embodiments of the present invention.

FIG. 9 is a conceptual structure 900 generated by modifying the conceptual structure of FIG. 8 via a business operational model analysis included in step 308 of FIG. 3, in accordance with embodiments of the present invention. Conceptual structure 900 includes an updated learning system 902 that includes the same conceptual components 602-616, 804 and 806 included in learning system 802 (see FIG. 8). As applied to the learning solution example, step 308 (see FIG. 3) analyzes the dynamic interactions among the different elements of the solution, including conceptual components and users. The step 308 (see FIG. 3) analysis is based on a business operational model created by one or more business stakeholders. For example, the business operational model for a student accessing learning material specifies the following steps that a student follows to access learning content:

1. Student logs into the learning solution.
2. Student accesses the list of assigned learning content.
3. Student selects the learning content to access.
4. Student accesses learning content.
5. Student logs off from the learning solution.

Analysis of the operational model presented above identifies the need for a security control component. Thus, step 308 (see FIG. 3) includes adding a security control conceptual component 908 within learning system 902 in conceptual structure 900. The operational concepts documentation describes the functions needed to execute the operational model presented above.

Using the exemplary business operational model steps presented above, several functions needed within an updated student system 904 are identified in step 308 (see FIG. 3). Step 308 (see FIG. 3) adds the following identified conceptual components to system 904: access learning content 910, access list of assigned learning content 912, access historical information 914 and security control 916. The list presented below includes functions that are identified as being needed within system 904. The list also includes corresponding conceptual components in parentheses. A description of each function in system 904 includes, for example, text, block diagrams, flow charts, sequence diagrams, state diagrams, and other forms of illustration and description as appropriate.

The functions identified as being needed by updated student system 904, as a result of an analysis of the business operational model for a scenario that involves a student accessing a learning content from the list of assigned learning content, are listed below:

1. Log on (security control 916)
2. Access list of assigned learning content (access list of assigned learning content 912)
3. Select learning content to access (access list of assigned learning content 912)
4. Access learning content (access learning content 910)
5. Log off (security control 916)

Using a similar analysis of the operational model for instructor access, functions needed within updated instructor system 906 are identified along with corresponding conceptual components. These corresponding conceptual components are added to system 906 and include: access learning content 918, author new learning content 920, enroll students 922, search for learning content 924, create reports 926 and security control 928. Similar to system 904, a description of each function in system 906 includes, for example, text, block diagrams, flow charts, sequence diagrams, state diagrams, and other forms of illustration and description as appropriate.

The aforementioned functions relative to systems 904 and 906 must be added to the operational concepts description created in step 318 (see FIG. 3). Adding to the operational concepts description in the learning solution example is described in detail below relative to FIG. 13.

7.5 Internal Process and Algorithm Analysis

Figure 10:
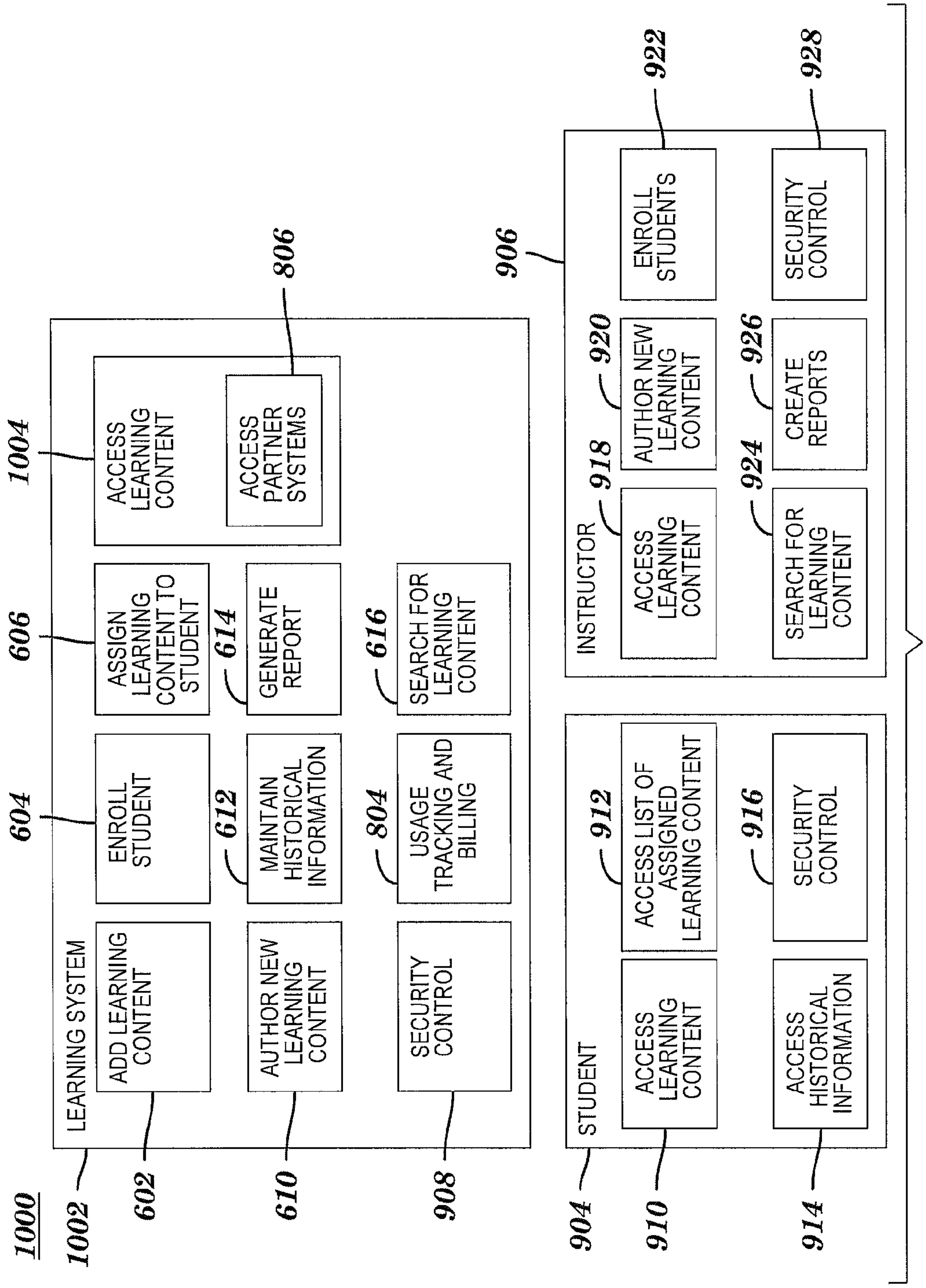
FIG. 10 is a conceptual structure generated by modifying the conceptual structure of FIG. 9 via an internal process and algorithm analysis included in the process of FIG. 3, in accordance with embodiments of the present invention.

FIG. 10 is a conceptual structure 1000 generated by modifying the conceptual structure of FIG. 9 via an internal process and algorithm analysis included in step 310 of FIG. 3, in accordance with embodiments of the present invention. Compared to the conceptual structure in FIG. 9, conceptual structure 1000 includes the same conceptual components 602, 604, 606, 610, 612, 614, 616, 804, 806 and 908 in an updated learning system 1002. Also compared to the conceptual structure in FIG. 9, conceptual structure 1002 includes the same student system 904 and instructor system 906, and the same system components 910-928.

As applied to the learning solution example, step 310 (see FIG. 3) examines the internal processes and algorithms needed to enable the operation of the conceptual components of learning system 1002 and student and instructor systems 904 and 906. For example, conceptual structure 900 (see FIG. 9) shows two conceptual components—access learning content 608 (see FIG. 9) and access partner systems 806 (see FIG. 9). A closer examination in step 310 (see FIG. 3) of the internal process needed to support access to learning content indicates that there are shared processing steps involved in accessing learning content whether the content is coming from an internal content repository or from partner learning systems. In step 310 (see FIG. 3), the access partner systems conceptual component 806 is therefore nested within an updated access learning content conceptual component 1004, thereby clarifying that access partner systems 806 is actually a subcomponent within access learning content conceptual component 1004. This nesting in access learning content 1004 is what makes learning system 1002 an updated version of learning system 902 (see FIG. 9).

7.6 Communication Needs Analysis

Figure 11:
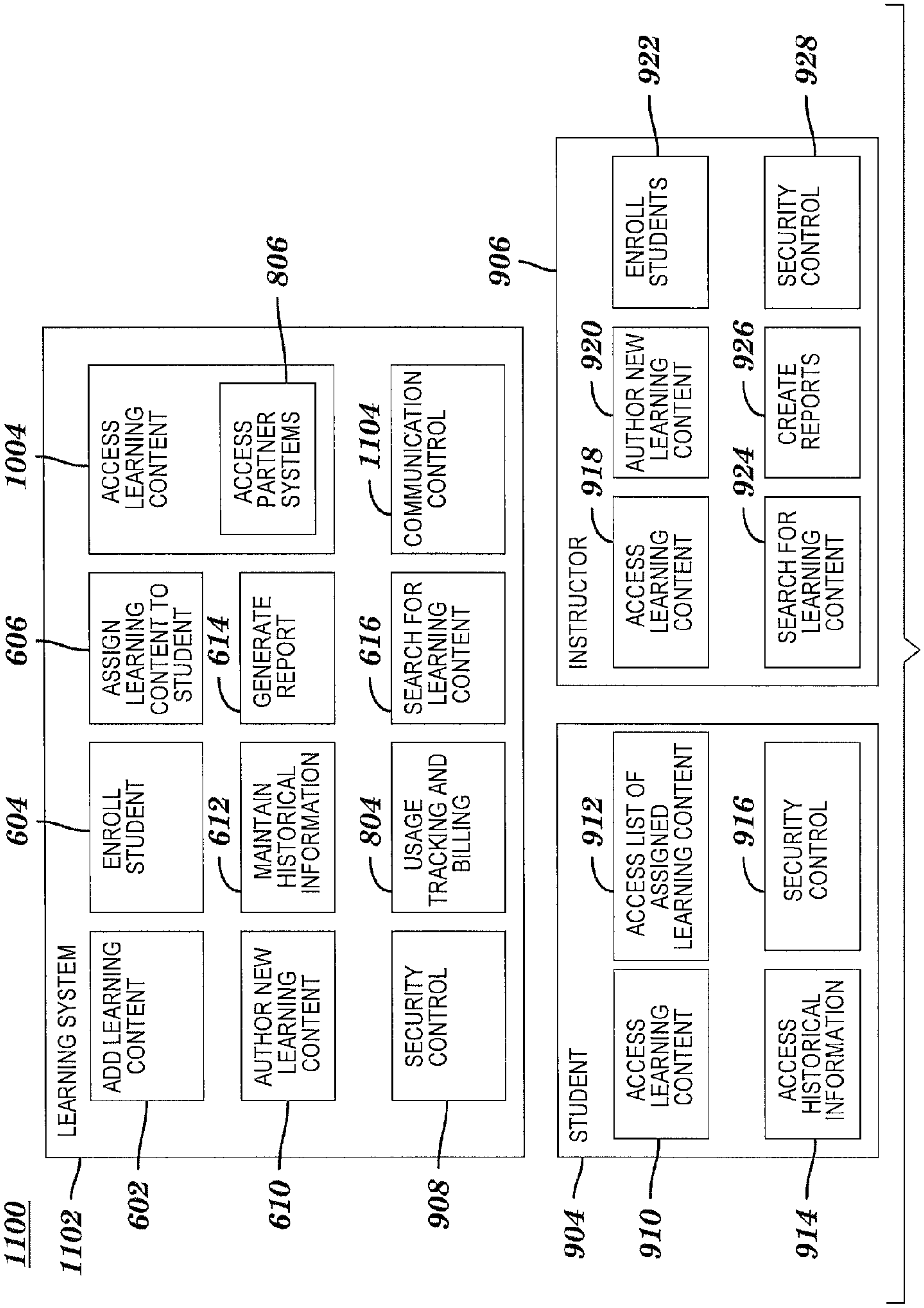
FIG. 11 is a conceptual structure generated by modifying the conceptual structure of FIG. 10 via a communication needs analysis included in the process of FIG. 3, in accordance with embodiments of the present invention.

FIG. 11 is a conceptual structure 1100 generated by modifying the conceptual structure of FIG. 10 via a communication needs analysis included in step 312 of FIG. 3, in accordance with embodiments of the present invention. Compared to the conceptual structure in FIG. 10, conceptual structure 1100 includes the same conceptual components 602, 604, 606, 610, 612, 614, 616, 804, 806, 908 and 1004 in an updated learning system 1102. Also compared to the conceptual structure in FIG. 10, conceptual structure 1100 includes the same student system 904 and instructor system 906, and the same system components 910-928.

As applied to the learning solution example, step 312 (see FIG. 3) analyzes the networking and content delivery requirements. Note that for the conceptual model being developed, the only communication needs that are considered are the communication needs that are significant from the perspective of the business stakeholder for the learning solution. Technical infrastructure requirements for networking and content delivery are not included in the conceptual model for the learning solution. If the system being modeled is a browser application, then a conceptual component is included that supports different communication protocols such as Hypertext Transfer Protocol (HTTP) and Secure Sockets Layer (SSL). Likewise, if the system being modeled is a PDA device, then conceptual components are included that support appropriate networking protocols such as WiFi and Code Division Multiple Access (CDMA). In the learning solution example, students access learning system 1102 over the Internet using any one of several end-user devices such as desktops, laptops, PDAs, and mobile phones. Instructors access learning system 1102 using web browsers on their desktop or laptop computers only. Furthermore, learning content must be formatted appropriate to the end-user device over which students access learning content. Step 312 (see FIG. 3) adds to learning system 1102 a communication control conceptual component 1104 that supports the aforementioned communication conditions. The operational concepts documentation (see step 318 of FIG. 3) describes how communication control conceptual component 1104 interacts with other conceptual components and their functions in order to support the aforementioned communication requirements.

7.7 Information Needs Analysis

Figure 12:
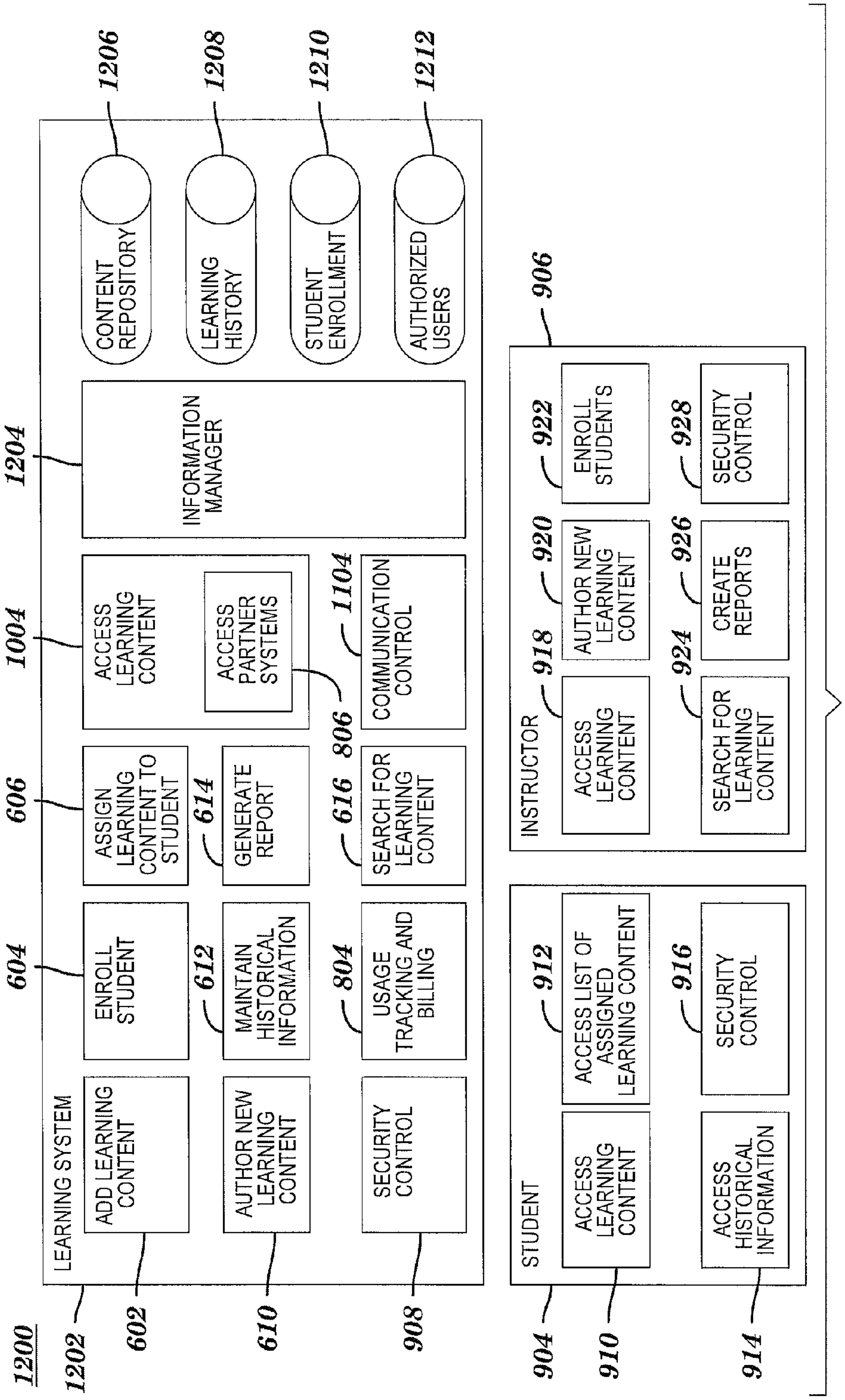
FIG. 12 is a conceptual structure generated by modifying the conceptual structure of FIG. 11 via an information needs analysis included in the process of FIG. 3, in accordance with embodiments of the present invention.

FIG. 12 is a conceptual structure 1200 generated by modifying the conceptual structure of FIG. 11 via an information needs analysis included in step 314 of FIG. 3, in accordance with embodiments of the present invention. Compared to the conceptual structure in FIG. 11, conceptual structure 1200 includes the same conceptual components 602, 604, 606, 610, 612, 614, 616, 804, 806, 908, 1004 and 1104 in an updated learning system 1202. Also compared to the conceptual structure in FIG. 11, conceptual structure 1200 includes the same student system 904 and instructor system 906, and the same system components 910-928.

As applied to the learning solution example, in step 314 (see FIG. 3) the information needs at the system-level as well as at the level of each of the conceptual components and their functions are examined, collected, and organized as operations that an information manager conceptual component 1204 supports. Various information repositories that information manager 1204 relies on to support the information-related functions are also identified and defined. These information repositories include a content repository 1206 and repositories for learning history 1208, student enrolment 1210, and authorized users 1212. In step 314 (see FIG. 3), information manager 1204 and repositories 1206, 1208, 1210 and 1212 are added to learning system 1202.

7.8 Non-Functional Requirements Analysis

Figure 13:
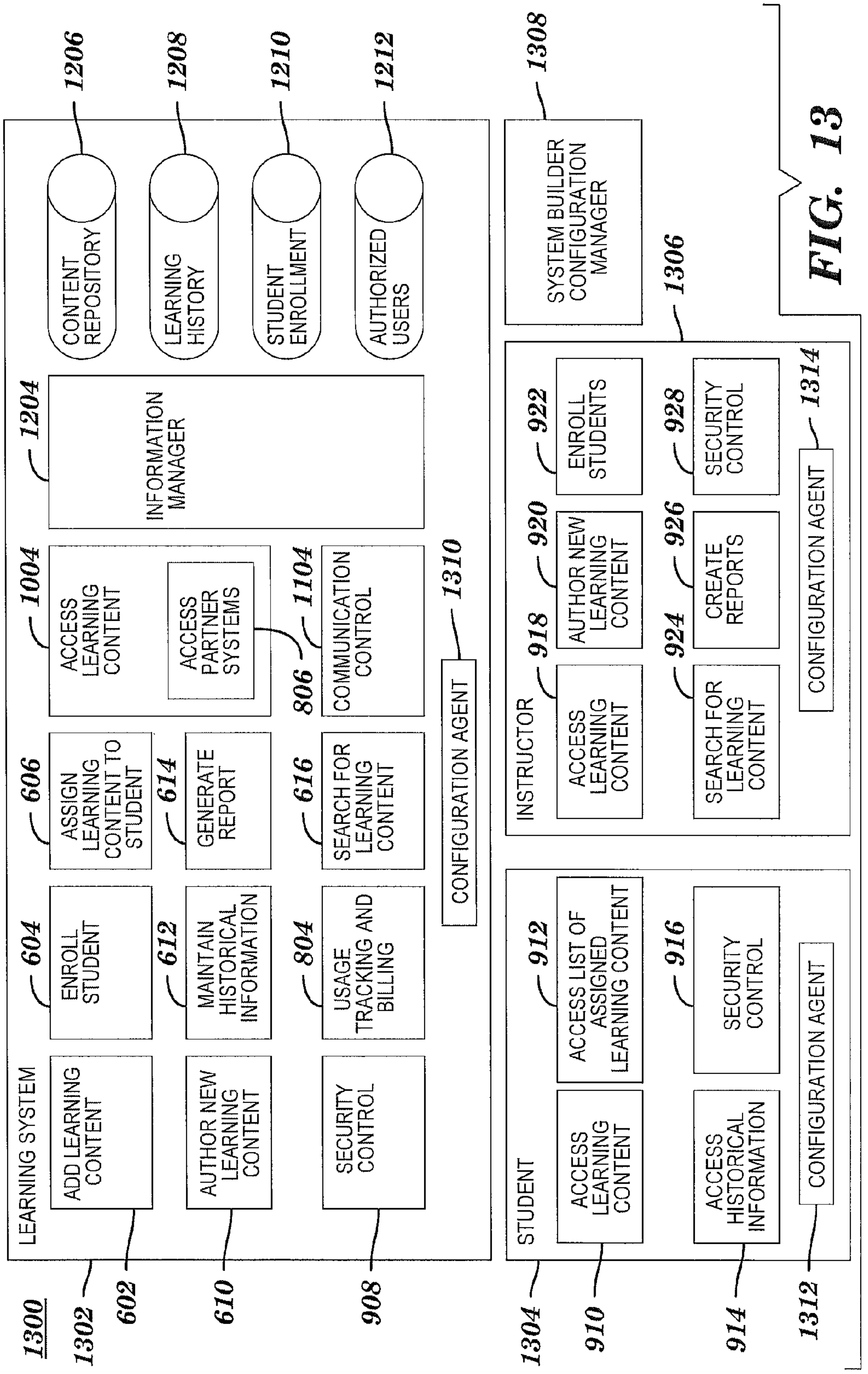
FIG. 13 is a conceptual structure generated by modifying the conceptual structure of FIG. 12 via a non-functional requirements analysis included in the process of FIG. 3, in accordance with embodiments of the present invention.

FIG. 13 is a conceptual structure 1300 generated by modifying the conceptual structure of FIG. 12 via a non-functional requirements analysis included in step 316 of FIG. 3, in accordance with embodiments of the present invention. Compared to the conceptual structure in FIG. 12, conceptual structure 1300 includes the same conceptual components 602, 604, 606, 610, 612, 614, 616, 804, 806, 908, 1004, 1104, 1204, 1206, 1208, 1210 and 1212 in an updated learning system 1302. Step 316 (see FIG. 3) updates learning system 1302 by adding a configuration agent 1310. Also compared to the conceptual structure in FIG. 12, conceptual structure 1300 includes an updated student system 1304, an updated instructor system 1306 and a newly added system builder configuration manager 1308 (a.k.a. configuration manager system). Conceptual components 910-916 (see also FIG. 12) are included in system 1304; conceptual components 918-928 (see also FIG. 12) are included in system 1306. In step 316 (see FIG. 3), a configuration agent 1312 is added to system 1304 and a configuration agent 1314 is added to system 1306. For simplicity, FIG. 13 does not show conceptual components within configuration manager system 1308; however, it will be apparent to those skilled in the art that the methods described herein for adding the conceptual components depicted in FIG. 13 can be adapted to add conceptual components to configuration manager system 1308.

In step 316 (see FIG. 3), the conceptual structure is refined based on non-functional requirements specified for the solution. In the learning solution example, there is one non-functional requirement specified. The non-functional requirement specifies that the solution must be customizable for private-labelling purposes. Analysis of this non-functional requirement in step 316 (see FIG. 3) leads to the addition of a new configuration manager system 1308 that is to be used by persons playing the role of System Builder during the system building process. The System Builder customizes the look-and-feel of systems 1302, 1304, 1306 and 1308 using pre-defined customization operations. Further changes caused by performing step 316 (see FIG. 3) include adding configuration agents 1310, 1312 and 1314 into learning system 1302, student system 1304 and instructor system 1306, respectively.

7.9 Operational Concepts Description

Conceptual structure 1300 identifies the conceptual components in the learning solution. Conceptual structure 1300 also identifies the systems (e.g., systems 1302, 1304 and 1306) and the systems' conceptual components. Conceptual structure 1300 is a business-aligned description of the structure and components in the learning solution. The conceptual components included in conceptual structure 1300 must interact in a pre-specified way to support the business purposes of the learning solution. Using step 318 (see FIG. 3) and the process of FIG. 4, operational concepts related to conceptual structure 1300 are described. Relative to FIG. 4, steps 404-414 are repeated for each conceptual component included in learning system 1302. These steps 404-414 (see FIG. 4) are also repeated for student system 1304 and instructor system 1306, and the conceptual components included in systems 1304 and 1306. The following subsections 7.9.1-7.9.7 illustrate the results from step 402 (see FIG. 4) and the results of steps 404-414 for several conceptual components. Again, step 406 (see FIG. 4) is further detailed by the process of FIG. 5.

7.9.1 Create/Update High-Level Overview of Conceptual Structure

In step 402 (see FIG. 4) applied to describing the operational concepts for the learning solution example, an overall description of the conceptual structure is developed. The online learning solution is a web-based solution that allows anytime, anywhere access to anyone on the Internet to online multimedia learning content. The conceptual structure of the learning solution is shown as conceptual structure 1300 in FIG. 13. The learning solution consists of a base learning system 1302 and two additional systems 1304 and 1306, called student and instructor, respectively. Various components in learning system 1302 and the two systems 1304 and 1306 are defined as shown in FIG. 13 in order to provide a modular view of the conceptual structure of the overall learning solution.

Figure 14:
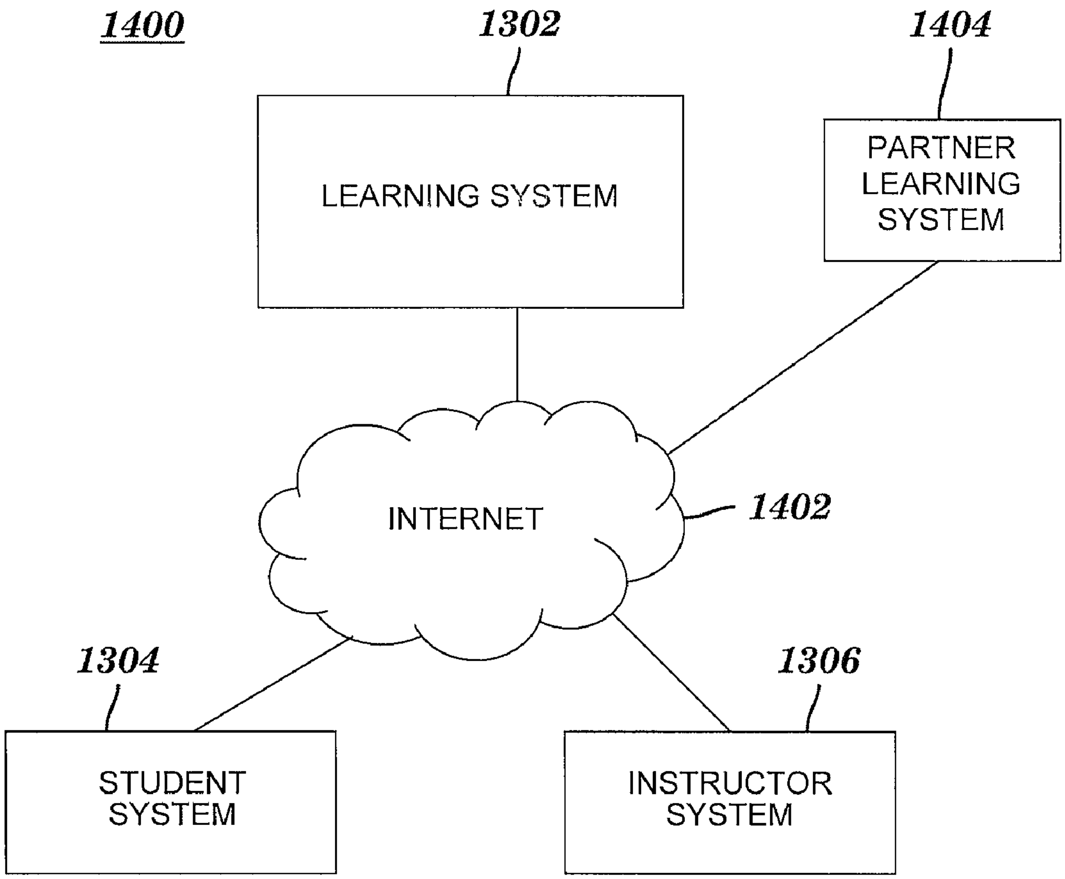
FIG. 14 is a block diagram of an exemplary web-based system that includes the conceptual structure of FIG. 13 and that is created in the process of FIG. 4, in accordance with embodiments of the present invention.

FIG. 14 is a block diagram of an exemplary web-based solution 1400 that includes the conceptual structure of FIG. 13 and that is created in the process of FIG. 4, in accordance with embodiments of the present invention. System 1400 illustrates how the different systems 1302, 1304 and 1306 integrate via Internet 1402 with one another and with other external systems such as a partner learning system 1404.

Instructor system 1306 allows instructors to perform various functions such as:

- Add learning content into learning system 1302
- Enroll students into learning system 1302
- Assign learning content for students
- Author new learning content
- Generate reports on learning activities by students for overall management of the learning process.

Instructors connect to learning system 1302 over the Internet 1402 and perform the different functions identified above.

Student system 1304 allows students to access and utilize learning content for learning purposes. The different functions supported for students include:

- Access the list of assigned learning content
- Select and access a learning content from the list
- View historical information on learning content assigned and accessed and re-access any of the content already accessed in the past.

Instructors and students access learning system 1302 from anywhere as long as they have connectivity to the Internet 1402. Specific bandwidth requirements apply for the Internet connections, depending upon specific implementations of learning system 1302 and specific needs of the learning content used. While the learning solution requires instructors to access and utilize the learning solution using a web browser application on a desktop or laptop computer, students can also use PDAs and mobile telephones to access and utilize the learning solution. The rest of the operational concepts documentation provides a conceptual description of the different parts (i.e., components) of the learning solution and how they interact with one another to perform the necessary functions. The operational concepts also describe important non-functional aspects of the learning solution that are essential to support pre-specified uses of the solution.

Steps 404-414 (see FIG. 4) as applied to the access learning content conceptual component 1004 (see FIG. 13) of the learning solution example are illustrated in the following subsections.

7.9.2 Describe the Purpose of the Conceptual Component

In step 404 (see FIG. 4) as applied to the operational concepts description in the learning solution example, access learning content conceptual component 1004 (see FIG. 13) is described as being responsible for fetching a learning content from content repository 1206 (see FIG. 13) and delivering it to the user (i.e., requester). Each learning content item is identified by a unique identifier (a.k.a. unique learning content identifier) in learning system 1302 (see FIG. 13). Using the unique identifier, the access learning content conceptual component 1004 (see FIG. 13) fetches the learning content from repository 1206 (see FIG. 13). When the learning content is located in a partner learning system 1404 (see FIG. 14), component 1004 (see FIG. 13) invokes access partner systems sub-component 806 (see FIG. 13) to fetch the learning content from the appropriate partner system (i.e., partner learning system 1404 of FIG. 14).

7.9.3 Describe the Functions and Internal Processes for the Conceptual Component In step 406 (see FIG. 4) as applied to the operational concepts description for the learning solution example, the following functions supported by access learning content conceptual component 1004 (see FIG. 13) are identified and described:

Fetch Learning Content

Fetch Learning Content description

Each of the functions listed above is described using the process of FIG. 5. Subsections 7.9.3.1-7.9.3.5 illustrate the outcomes of steps 502-510, respectively, of FIG. 5, using the Fetch Learning Content function as an example.

7.9.3.1 Describe the Purpose of the Function

This subsection describes the outcome of step 502 (see FIG. 5) as applied to the Fetch Learning Content function. The Fetch Learning Content function locates the requested learning content and delivers the related content files to the requester.

7.9.3.2 Describe the Inputs and Outputs of the Function

This subsection describes the outcome of step 504 (see FIG. 5) as applied to the Fetch Learning Content function. The input for the Fetch Learning Content function is the unique learning content identifier. A detailed description of the structure of the unique learning content identifier is provided in a corresponding section of the operational concepts document.

The output from the Learning Content function is one or more files delivered to the requestor. The files that can be returned to the requestor and the conditions under which the files are returned are described in a corresponding section of the operational concepts document.

7.9.3.3 Describe the Steps Involved in the Internal Process to Perform the Function This subsection describes the outcome of step 506 (see FIG. 5) as applied to the Fetch Learning Content function. The following steps are performed to perform the Fetch Learning Content function (i.e., to fetch the learning content):

1. The unique identifier for the learning content is extracted from the input to the Fetch Learning Content function.
2. An internal decoding function is applied on the unique identifier to determine if the learning content is in the local content repository 1206 (see FIG. 13) or located in a partner system 1404 (see FIG. 14).
3. If the learning content is located in the local content repository 1206 (see FIG. 13), the files for the learning content are requested from information manager 1204 (see FIG. 13).
4. If the learning content is located in a partner system 1404 (see FIG. 14), the files for the learning content are requested from the partner system 1404 (see FIG. 14) through the access partner systems conceptual component 806 (see FIG. 13).
5. The files for the learning content are returned to the requester.

Figure 15:
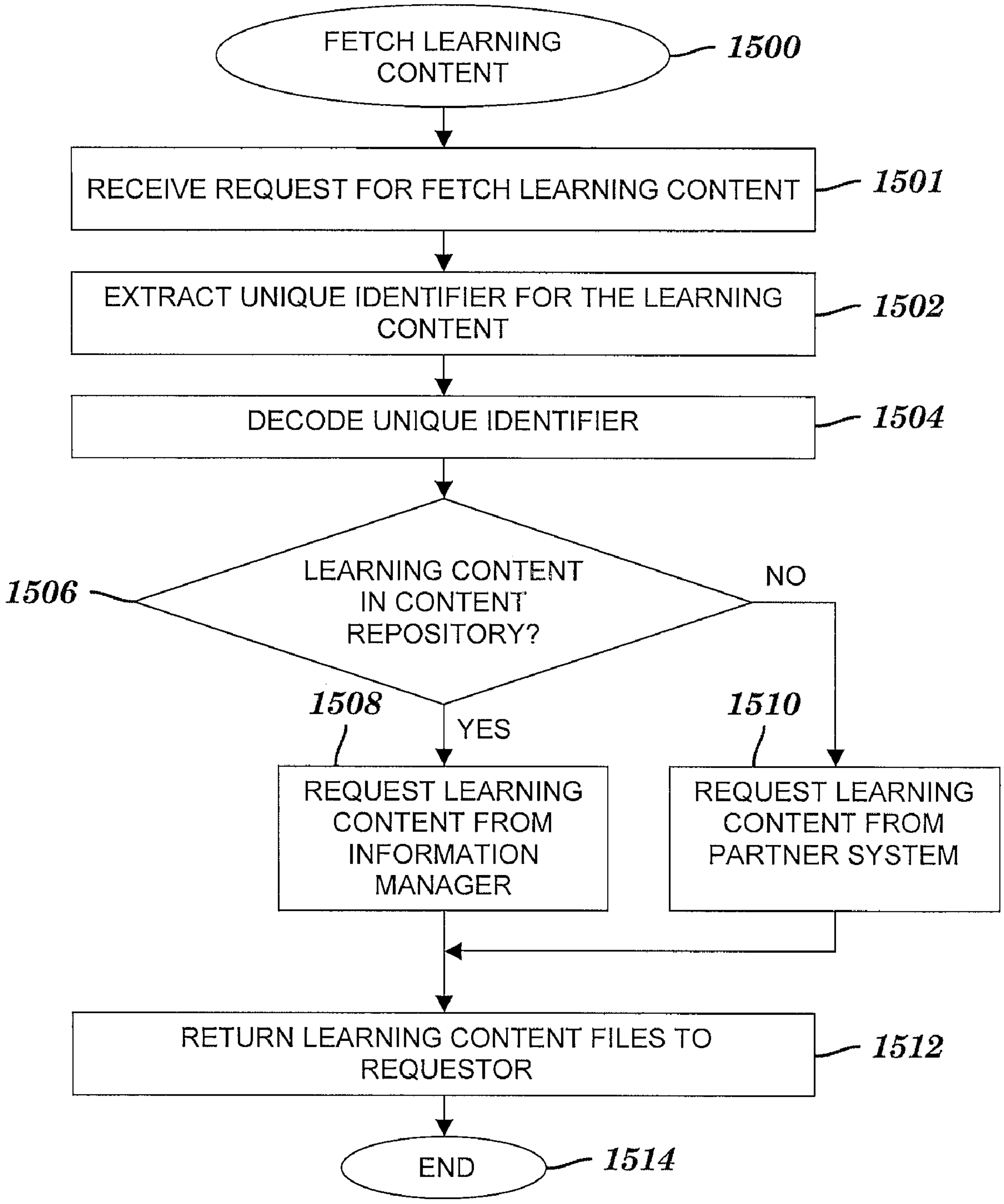
FIG. 15 is a flow diagram of an exemplary business function described in the process of FIG. 5, in accordance with embodiments of the present invention.

As one example, the steps listed above are included in the Fetch Learning Content flow diagram in FIG. 15. The Fetch Learning Content process starts at step 1500. In step 1502, a request to fetch learning content is received from a requester. In step 1504, the unique identifier for the requested learning content is extracted from the input to the Fetch Learning Content function (see step 1 listed above). In step 1504, the unique identifier extracted in step 1502 is decoded by the internal decoding function (see step 2 listed above). In step 1506, learning system 1302 (see FIG. 13) determines whether the requested learning content is in content repository 1206 (see FIG. 13). If step 1506 determines that the requested learning content is in repository 1206 (see FIG. 13), then in step 1508 the learning content files corresponding to the requested learning content is requested from information manager 1204 (see FIG. 13) (see step 3 listed above) and learning system 1302 (see FIG. 13) returns the learning content files to the requestor in step 1512 (see step 5 listed above).

Returning to inquiry step 1506, if it is determined that the requested learning content is not in an internal content repository, then the requested learning content resides in learning partner system 1404 (see FIG. 14), access partner systems subcomponent 806 requests the corresponding learning content files from learning partner system 1404 (see FIG. 14), and subcomponent 806 returns the learning content files to the requestor in step 1512.

Following step 1512, the process of FIG. 15 ends at step 1514.

7.9.3.4 Describe the Information Management Needs of the Function

Figure 16:
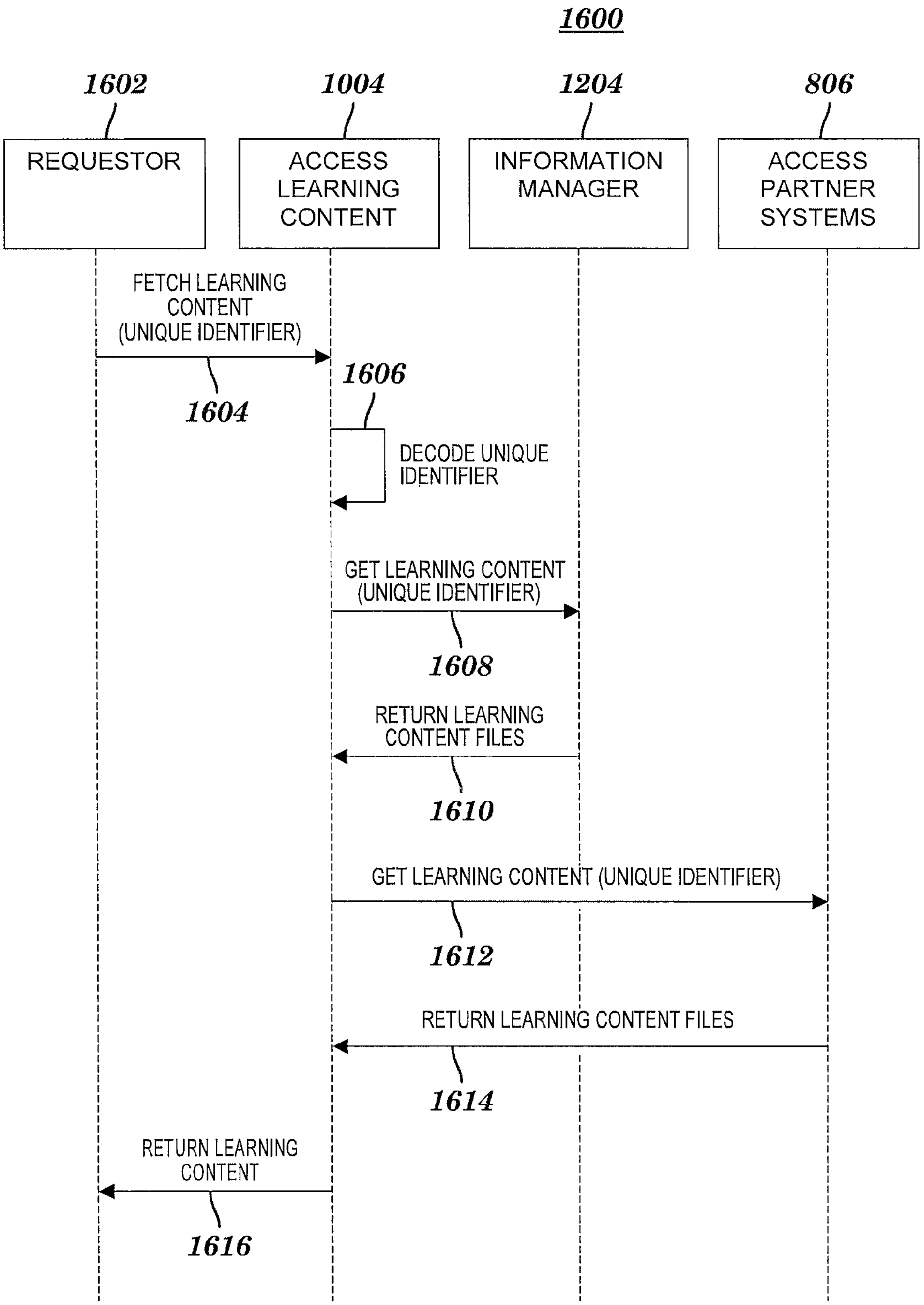
FIG. 16 is a sequence diagram of an exemplary function's operation described in the process of FIG. 5, in accordance with embodiments of the present invention.

This subsection describes the outcome of step 508 (see FIG. 5) as applied to the Fetch Learning Content function. The Fetch Learning Content function requires the following function to be supported by information manager 1204 (see FIG. 13):

Get learning content files 7.9.3.5 Describe the Operation of the Function in Terms of the Dynamic Interactions with Other Conceptual Components This subsection describes the outcome of step 510 (see FIG. 5) as applied to the Fetch Learning Content function. FIG. 16 is a sequence diagram 1600 that describes the operation of the Fetch Learning Content function in terms of interactions among a requestor 1602 who requests learning content, access learning content conceptual component 1004, information manager 1204 and access partner systems subcomponent 806. In step 1604, a request from requestor 1602 to fetch learning content is received by access learning content conceptual component 1004. The request includes a unique identifier for the requested learning content. In step 1606, access learning content conceptual component 1004 decodes the unique identifier to determine whether the learning content files corresponding to the requested learning content reside in an internal content repository (i.e., a content repository internal to learning system 1302 of FIG. 13) or in partner learning system 1404 (see FIG. 14). If the learning content files reside in the internal content repository, then in step 1608, access learning content conceptual component 1004 requests the learning content files from information manager 1204 and the information manager returns the requested learning content files to the access learning content conceptual component in step 1610. If, however, the learning content files reside in partner learning system 1404 (see FIG. 14), then in step 1612, access learning content conceptual component 1004 requests the learning content files from access partner systems subcomponent 806 and the access partner systems subcomponent returns the learning content files to the access learning content conceptual component in step 1614. Following step 1610 and step 1614, the learning content files are received by requester 1602 from access learning content conceptual component 1004.

7.9.4 Describe the Information Management Needs of the Conceptual Component

Figure 17:
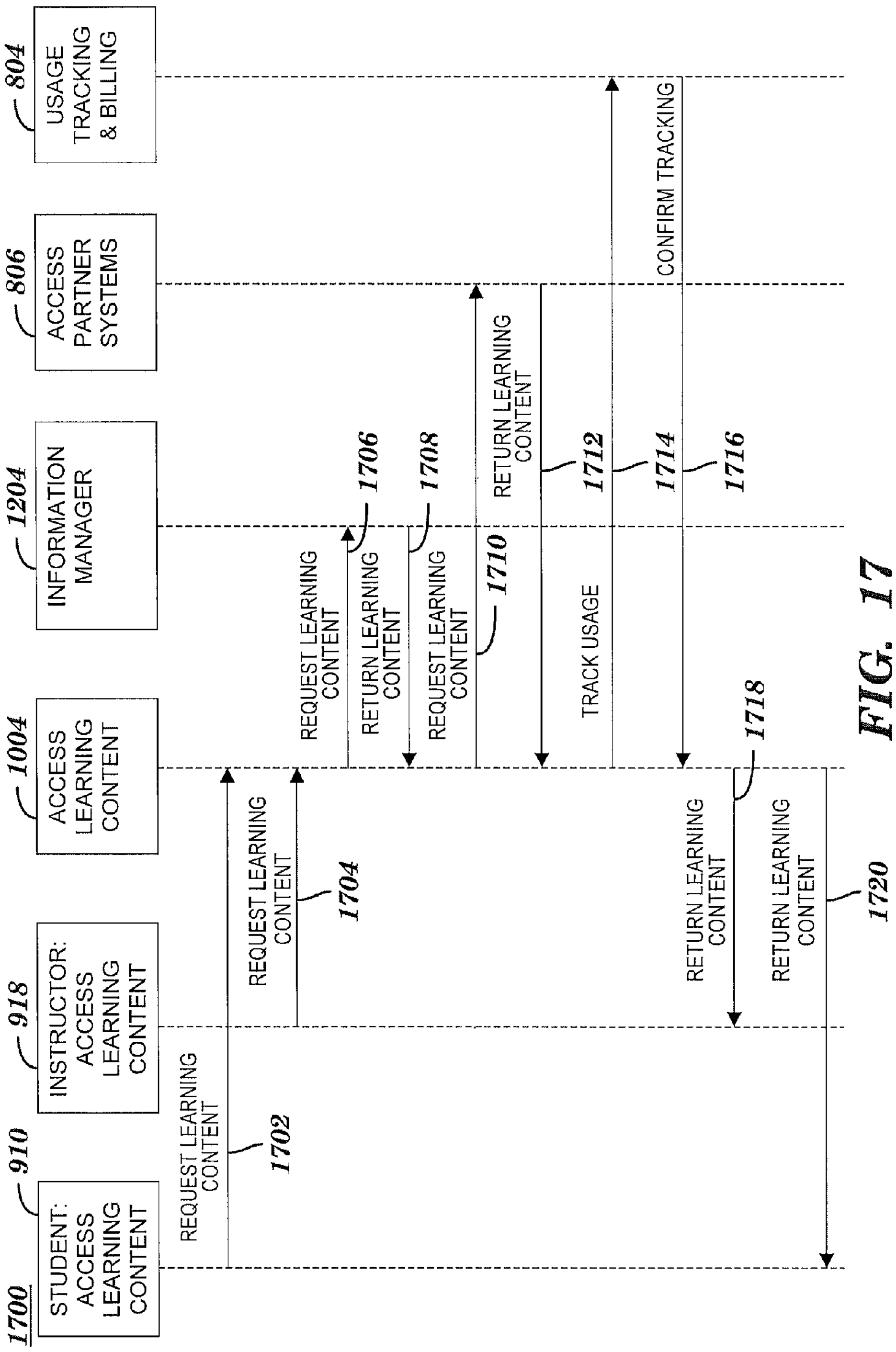
FIG. 17 is a sequence diagram of an exemplary conceptual component's operation described in the process of FIG. 4, in accordance with embodiments of the present invention.

In step 408 (see FIG. 4) as applied to the operational concepts description for the learning solution example, the information needs are identified and described for each of the functions described in step 406 (see FIG. 4) are collected. A consolidated list of the functions described in step 406 (see FIG. 4) is provided. There is no need to repeat the description of each of the functions again. In addition, if there are any additional information management needs that are over and above those identified for each of the functions, then those information management needs are described in step 408 (see FIG. 4). In the learning solution example, the information management needs for access learning content conceptual component 1004 are described as follows:

Access learning content conceptual component 1004 (see FIG. 13) requires the following functions to be supported by information manager 1204 (see FIG. 13):

Get learning content files a Get learning content description 7.9.5 Describe the Operation of the Conceptual Component, Focusing on the Dynamic Interactions with other Conceptual Components In step 410 (see FIG. 4), a high-level description of the different interactions between the conceptual component being described and other conceptual components, systems and subsystems is provided. In the learning solution example, step 410 (see FIG. 4) includes describing the interactions between access learning content conceptual component 1004 (see FIG. 13) and other conceptual components of learning system 1302 (see FIG. 13) and systems external to learning system 1302 (see FIG. 13). FIG. 17 is a sequence diagram 1700 that provides a high-level description of interactions between access learning content conceptual component 1004 and the following conceptual components: student access learning content 910 (i.e., the access learning content conceptual component included in student system 1304 of FIG. 13), instructor access learning content 918 (i.e., the access learning content conceptual component included in instructor system 1306 of FIG. 13), information manager 1204, access partner systems 806 and usage tracking and billing 804.

Student-initiated request for learning content: In step 1702, access learning content conceptual component 1004 receives a request for learning content from student access learning content conceptual component 910. If the learning content files corresponding to the requested learning content is located in an internal content repository (e.g., repository 1206 of FIG. 13), then in step 1706, access learning content conceptual component 1004 requests the learning content files from information manager 1204, and information manager 1204 returns the requested learning content files to access learning content conceptual component 1004 in step 1708.

If the learning content files are instead located in a partner system (e.g., partner learning system 1404 of FIG. 14), then in step 1710, access learning content conceptual component 1004 requests the learning content files from access partner systems subcomponent 806 and access partner systems subcomponent 806 returns the requested learning content files to access learning content conceptual component 1004 in step 1712.

Steps 1712 and 1714 are described in subsection 7.9.6. In step 1720, access learning content conceptual component 1004 returns the requested learning content files to student access learning content conceptual component 910.

Instructor-initiated request for learning content: In step 1704, access learning content conceptual component 1004 receives a request for learning content from instructor access learning content conceptual component 918. As indicated above relative to the student-initiated learning content request, either steps 1706-1708 or steps 1710-1712 are performed to request and retrieve the learning content files corresponding to the requested learning content. Again, steps 1712 and 1716 are described below in subsection 7.9.6. In step 1718, access learning content conceptual component 1004 returns the requested learning content files to instructor access learning content conceptual component 918.

7.9.6 Describe the Appropriate Business Model Implications for the Conceptual Component In step 412 (see FIG. 4), as applied to the operational concepts description for the learning solution example, the business model implications are described as follows:

The business model specified indicates via business rules that access to learning content may incur a charge depending upon whether the learning content is instructor-created, from a third-party learning system, etc. These business rules are managed by usage tracking and billing conceptual component 804. The business model, however, requires that access learning content conceptual component 1004 reports all learning content returned to requester 1602 (see FIG. 16) to be reported to usage tracking and billing conceptual component 804. In step 1712 of sequence diagram 1700, access learning content conceptual component 1004 tracks usage by reporting the requested learning content to usage tracking and billing conceptual component 804. In step 1716, access learning content conceptual component 1004 receives a confirmation of the step 1712 tracking from usage tracking and billing conceptual component 804.

7.9.7 Describe Non-Functional Requirements for the Conceptual Component

In step 414 (see FIG. 4), as applied to the operational concepts description for the learning solution example, the non-functional requirements for access learning content conceptual component 1004 are described as follows:

The non-functional requirement specified in the learning solution example states that the solution must be customizable for private-labelling purposes. If there are specific customization capabilities within access learning content conceptual component 1004, these are described in step 414. The actual customization functions are performed by configuration manager system 1308 (see FIG. 13) in collaboration with configuration agent conceptual components 1310, 1312 and 1314 of FIG. 13 located in learning system 1302 (see FIG. 13), student system 1304 (see FIG. 13) and instructor system 1306 (see FIG. 13), respectively.

Computing System

Figure 18:
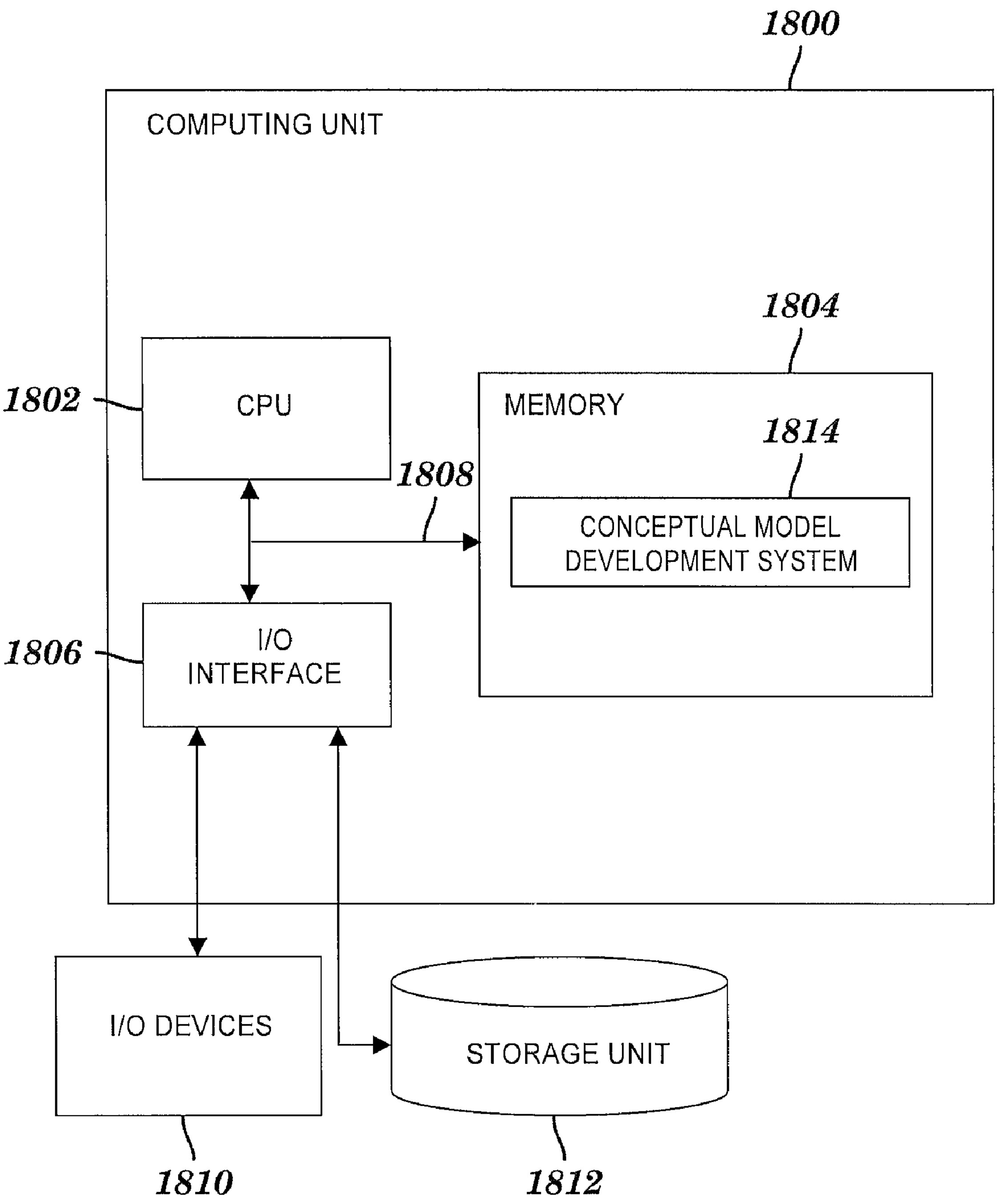
FIG. 18 is a block diagram of a computing system that implements the process of FIG. 3, in accordance with embodiments of the present invention.

FIG. 18 is a block diagram of a computing unit that implements the process of FIG. 3, in accordance with embodiments of the present invention. Computing unit 1800 generally comprises a central processing unit (CPU) 1802, a memory 1804, an input/output (I/O) interface 1806, a bus 1808, I/O devices 1810 and a storage unit 1812. CPU 1802 performs computation and control functions of computing unit 1800. CPU 1802 may comprise a single processing unit, or be distributed across one or more processing units in one or more locations (e.g., on a client and server).

Memory 1804 may comprise any known type of data storage and/or transmission media, including bulk storage, magnetic media, optical media, random access memory (RAM), read-only memory (ROM), a data cache, a data object, etc. Cache memory elements of memory 1804 provide temporary storage of at least some program code in order to reduce the number of times code must be retrieved from bulk storage during execution. Storage unit 1812 is, for example, a magnetic disk drive or an optical disk drive that stores data. Moreover, similar to CPU 1802, memory 1804 may reside at a single physical location, comprising one or more types of data storage, or be distributed across a plurality of physical systems in various forms. Further, memory 1804 can include data distributed across, for example, a LAN, WAN or storage area network (SAN) (not shown).

I/O interface 1806 comprises any system for exchanging information to or from an external source. I/O devices 1810 comprise any known type of external device, including a display monitor, keyboard, mouse, printer, speakers, handheld device, printer, facsimile, etc. Bus 1808 provides a communication link between each of the components in computing unit 1800, and may comprise any type of transmission link, including electrical, optical, wireless, etc.

I/O interface 1806 also allows computing unit 1800 to store and retrieve information (e.g., program instructions or data) from an auxiliary storage device (e.g., storage unit 1812). The auxiliary storage device may be a non-volatile storage device (e.g., a CD-ROM drive which receives a CD-ROM disk). Computing unit 1800 can store and retrieve information from other auxiliary storage devices (not shown), which can include a direct access storage device (DASD) (e.g., hard disk or floppy diskette), a magneto-optical disk drive, a tape drive, or a wireless communication device.

Memory 1804 includes computer program code 1814 for the conceptual model development process disclosed herein. Further, memory 1804 may include other systems not shown in FIG. 18, such as an operating system (e.g., Linux) that runs on CPU 1802 and provides control of various components within and/or connected to computing unit 1800.

The invention can take the form of an entirely hardware embodiment, an entirely software embodiment or an embodiment containing both hardware and software elements. In a preferred embodiment, the invention is implemented in software, which includes but is not limited to firmware, resident software, microcode, etc.

Furthermore, the invention can take the form of a computer program product accessible from a computer-usable or computer-readable medium providing program code 1814 for use by or in connection with a computing unit 1800 or any instruction execution system to provide and facilitate the capabilities of the present invention. For the purposes of this description, a computer-usable or computer-readable medium can be any apparatus that can contain, store, communicate, propagate, or transport the program for use by or in connection with the instruction execution system, apparatus, or device.

The medium can be an electronic, magnetic, optical, electromagnetic, infrared, or semiconductor system (or apparatus or device) or a propagation medium. Examples of a computer-readable medium include a semiconductor or solid state memory, magnetic tape, a removable computer diskette, RAM 1804, ROM, a rigid magnetic disk and an optical disk. Current examples of optical disks include compact disk—read-only memory (CD-ROM), compact disk—read/write (CD-R/W) and DVD.

Any of the components of the present invention can be deployed, managed, serviced, etc. by a service provider that offers to deploy or integrate computing infrastructure with respect to the method of developing a conceptual model to facilitate generating a business-aligned information technology system. Thus, the present invention discloses a process for supporting computer infrastructure, comprising integrating, hosting, maintaining and deploying computer-readable code into a computing system (e.g., computing unit 1800), wherein the code in combination with the computing unit is capable of performing a method of developing a conceptual model to facilitate generating a business-aligned information technology solution.

In another embodiment, the invention provides a business method that performs the process steps of the invention on a subscription, advertising and/or fee basis. That is, a service provider, such as a Solution Integrator, can offer to create, maintain, support, etc. a method of developing a conceptual model to facilitate generating a business-aligned information technology solution. In this case, the service provider can create, maintain, support, etc. a computer infrastructure that performs the process steps of the invention for one or more customers. In return, the service provider can receive payment from the customer(s) under a subscription and/or fee agreement, and/or the service provider can receive payment from the sale of advertising content to one or more third parties.

The flow diagrams depicted herein are provided by way of example. There may be variations to these diagrams or the steps (or operations) described herein without departing from the spirit of the invention. For instance, in certain cases, the steps may be performed in differing order, or steps may be added, deleted or modified. All of these variations are considered a part of the present invention as recited in the appended claims.

While embodiments of the present invention have been described herein for purposes of illustration, many modifications and changes will become apparent to those skilled in the art. Accordingly, the appended claims are intended to encompass all such modifications and changes as fall within the true spirit and scope of this invention. For example, the references to a business disclosed herein may be replaced with any organizational entity, regardless of whether the entity is a for-profit or a non-profit enterprise.

What is claimed is:

1. A method of developing an information technology solution via development of a conceptual model, said method comprising:

defining, by one or more business stakeholders associated with a business, a plurality of requirements of an information technology (IT) solution owned by said business, wherein said requirements indicate a plurality of functions of said business to be supported by said IT solution;

said one or more business stakeholders and one or more IT stakeholders associated with said business developing a conceptual model by developing a conceptual structure and subsequently developing a plurality of operational concepts, said conceptual model including said conceptual structure and a plurality of operational concepts and providing a representation of said IT solution, said conceptual structure including a plurality of conceptual components, said plurality of conceptual components being icons, forms, shapes and/or figures determined by outlines that modularly represent one or more IT systems, one or more hardware components of said one or more IT systems and one or more software components of said one or more IT systems, said one or more IT systems, said one or more hardware components and said one or more IT systems being manifestations (manifested conceptual components) of said plurality of conceptual components in an implementation of said IT solution, and said plurality of operational concepts indicating interactions among said manifested conceptual components to perform said plurality of functions of said business, wherein said developing said conceptual structure includes:

defining said conceptual structure based on a functional analysis of said plurality of functions of said business by said one or more business stakeholders and said one or more IT stakeholders; and subsequent to said defining said conceptual structure, refining said conceptual structure by:

refining said conceptual structure based on a first analysis of interactions of one or more users with said IT solution;

refining said conceptual structure based on a second analysis of a business model of said business;

refining said conceptual structure based on a third analysis of how said manifested conceptual components interact with each other to support a business operational model of said business, said business operational model being a description by said one or more business stakeholders of how said business operates to attain one or more operational goals of said business;

refining said conceptual structure based on a fourth analysis of one or more internal processes and one or more algorithms, said one or more internal processes associated with an operation of a set of manifested conceptual components included in said manifested conceptual components and with interactions therebetween, and said one or more algorithms associated with said operation of said set of manifested conceptual components and with said interactions therebetween;

refining said conceptual structure based on a fifth analysis of one or more requirements for communication among said manifested conceptual components, between said IT solution and one or more systems of said IT solution, and between said IT solution and one or more systems external to said IT solution;

refining said conceptual structure based on a sixth analysis of one or more requirements for capturing, storing, retrieving and managing information internal to said one or more systems of said IT solution; and refining said conceptual structure based on a seventh analysis of non-functional requirements of said IT solution, wherein a result of said refining said conceptual structure is a refinement of said conceptual structure, wherein said refinement includes a new conceptual component added to said plurality of conceptual components, wherein said refinement further includes a partition of a conceptual component of said plurality of conceptual components into two or more conceptual components that are added to said plurality of conceptual components and/or an aggregation of at least two conceptual components of said plurality of conceptual components into a new composite conceptual component added to said plurality of conceptual components, wherein said subsequently developing said plurality of operational concepts includes:

prior to developing an architecture and a design of said IT solution, generating a description of said plurality of operational concepts based on said refinement of said conceptual structure, said description including:

a first description of said plurality of conceptual components included in said refinement of said conceptual structure, a second description of said plurality of functions, said one or more internal processes, and said one or more algorithms supported by said manifested conceptual components represented by said plurality of conceptual components included in said refinement of said conceptual structure, a third description of information management needs of said manifested conceptual components represented by said plurality of conceptual components included in said refinement of said conceptual structure, a fourth description of how said manifested conceptual components represented by said plurality of conceptual components included in said refinement of said conceptual structure interact among themselves to perform said plurality of functions of said business, a fifth description of how said business model relates to an organization of said plurality of conceptual components included in said refinement of said conceptual structure, and a sixth description of how said non-functional requirements are addressed by said IT solution and by said manifested conceptual components represented by said plurality of components included in said refinement of said conceptual structure; and generating a diagram representing an overview of said IT solution and including said refinement of said conceptual structure;

a computing system retrieving said diagram representing said overview of said IT solution and including said refinement of said conceptual structure and generating a documentation that includes said diagram and said description of said plurality of operational concepts;

developing said architecture and said design of said IT solution by said one or more IT stakeholders based on said developed conceptual model and said documentation that includes said diagram representing said overview of said IT solution and said description of said plurality of operational concepts, wherein said description of said plurality of operational concepts included in said documentation that is a basis for said architecture and said design of said IT solution indicates said interactions among said manifested conceptual components to perform said plurality of functions of said business; and generating, by said one or more IT stakeholders, a second documentation of said architecture and said design of said IT solution.

2. The method of claim 1, wherein said refining said conceptual structure based on said seventh analysis of non-functional requirements includes analyzing a non-functional quality constraint selected from the group consisting of an availability constraint, a backup and recovery constraint, a capacity estimate and planning constraint, a configuration management constraint, a disaster recovery constraint, an extensibility constraint, a failure management constraint, a response time constraint, a reliability constraint, a scalability constraint, a security constraint, a service level agreement, a system management constraint, and a quality of service constraint, wherein said availability constraint indicates how said IT solution remains accessible to end users as pre-specified in response to a failure of said one or more IT systems, said one or more hardware components of said one or more IT systems or said one or more software components of said one or more IT systems, wherein said backup and recovery constraint indicates how information about functions of said IT solution are stored during normal operation and how said stored information is used to restore said normal operation subsequent to said failure of said one or more IT systems, said one or more hardware components or said one or more software components, wherein said capacity estimate and planning constraint indicates an ability of said IT solution to accommodate planned an unplanned increases in a usage load on said IT solution, wherein said configuration management constraint indicates how said IT solution is customized to meet specialized needs of said business and said end users, wherein said disaster recovery constraint indicates special operational procedures required for an operational continuity of said IT solution in response to disasters, wherein said extensibility constraint indicates special considerations that are required to add new functions of said business to said IT solution or to support new technologies, wherein said failure management constraint indicates how said IT solution responds to hardware, software and network failures, wherein said response time constraint indicates requirements of a response time of said IT solution to satisfy needs of said business, wherein said reliability constraint indicates an ability of said IT solution to support functionality in a predictable and reliable manner, wherein said scalability constraint indicates an ability to expand said IT solution to accommodate additions in the future of users, transactions, and data, wherein said security constraint indicates requirements for security including access control, authentication and identification, confidentiality, integrity, accountability, administration and configuration, and assurance and monitoring, wherein said service level agreement is a contractual agreement between said end users of said IT solution and an operator of said IT solution regarding operational goals of said one or more IT systems, wherein said system management constraint indicates capabilities of said IT solution to ensure a continued monitoring of said IT solution to ensure that availability is maintained and to allow updates of an infrastructure of said IT solution to occur in an orderly manner, and wherein said quality of service constraint indicates an ability of said IT solution to detect and compensate for potential overload situations.

3. The method of claim 1, wherein said third description of information management needs of said manifested conceptual components is independent of any technology used to implement said IT solution.

4. The method of claim 1, wherein said generating said description of said plurality of operational concepts includes generating said second description of said plurality of functions, said one or more internal processes, and said one or more algorithms supported by said manifested conceptual components by:

describing a purpose of a function of said plurality of functions;

describing one or more inputs and one or more outputs of said function;

describing an operation of an internal process of said one or more internal processes for performing said function;

describing one or more information management requirements of said function; and describing an operation of said function, said operation of said function based on one or more interactions of a manifested conceptual component of said manifested conceptual components with one or more other manifested conceptual components of said manifested of conceptual components.

5. The method of claim 1, wherein said refining said conceptual structure includes generating said plurality of conceptual components as a plurality of modular representations that are independent of any technology used to implement said one or more IT systems represented by said plurality of conceptual components.

6. A computing system comprising a processor coupled to a computer-readable memory unit, said memory unit comprising a software application, said software application comprising instructions that when executed by said processor implement the method of claim 1.

7. A computer program product, comprising a computer usable medium having computer readable program code embodied therein for developing an information technology solution via development of a conceptual model, said computer program product comprising:

computer-usable code for defining, by one or more business stakeholders associated with a business, a plurality of requirements of an information technology (IT) solution owned by said business, wherein said requirements indicate a plurality of functions of said business to be supported by said IT solution;

computer-usable code for developing a conceptual model by said one or more business stakeholders and one or more IT stakeholders associated with said business, wherein said computer-usable code for developing said conceptual model includes computer-usable code for developing a conceptual structure and computer-usable code for subsequently developing a plurality of operational concepts, said conceptual model including said conceptual structure and said plurality of operational concepts and providing a representation of said IT solution, said conceptual structure including a plurality of conceptual components, said plurality of conceptual components being icons, forms, shapes and/or figures determined by outlines that modularly represent one or more IT systems, one or more hardware components of said one or more IT systems and one or more software components of said one or more IT systems, said one or more IT systems, said one or more hardware components and said one or more IT systems being manifestations (manifested conceptual components) of said plurality of conceptual components in an implementation of said IT solution, and said plurality of operational concepts indicating interactions among said manifested conceptual components to perform said plurality of functions of said business, wherein said developing said conceptual structure includes:

defining said conceptual structure based on a functional analysis of said plurality of functions of said business by said one or more business stakeholders and said one or more IT stakeholders; and subsequent to said defining said conceptual structure, refining said conceptual structure by:

refining said conceptual structure based on a first analysis of interactions of one or more users with said IT solution;

refining said conceptual structure based on a second analysis of a business model of said business;

refining said conceptual structure based on a third analysis of how said manifested conceptual components interact with each other to support a business operational model of said business, said business operational model being a description by said one or more business stakeholders of how said business operates to attain one or more operational goals of said business;

refining said conceptual structure based on a fourth analysis of one or more internal processes and one or more algorithms, said one or more internal processes associated with an operation of a set of manifested conceptual components included in said manifested conceptual components and with interactions therebetween, and said one or more algorithms associated with said operation of said set of manifested conceptual components and with said interactions therebetween;

refining said conceptual structure based on a fifth analysis of one or more requirements for communication among said manifested conceptual components, between said IT solution and one or more systems of said IT solution, and between said IT solution and one or more systems external to said IT solution;

refining said conceptual structure based on a sixth analysis of one or more requirements for capturing, storing, retrieving and managing information internal to said one or more systems of said IT solution; and refining said conceptual structure based on a seventh analysis of non-functional requirements of said IT solution, wherein a result of said refining said conceptual structure is a refinement of said conceptual structure, wherein said refinement includes a new conceptual component added to said plurality of conceptual components, wherein said refinement further includes a partition of a conceptual component of said plurality of conceptual components into two or more conceptual components that are added to said plurality of conceptual components and/or an aggregation of at least two conceptual components of said plurality of conceptual components into a new composite conceptual component added to said plurality of conceptual components, wherein said subsequently developing said plurality of operational concepts includes:

prior to developing an architecture and a design of said IT solution, generating a description of said plurality of operational concepts based on said refinement of said conceptual structure, said description including:

a first description of said plurality of conceptual components included in said refinement of said conceptual structure, a second description of said plurality of functions, said one or more internal processes, and said one or more algorithms supported by said manifested conceptual components represented by said plurality of conceptual components included in said refinement of said conceptual structure, a third description of information management needs of said manifested conceptual components represented by said plurality of conceptual components included in said refinement of said conceptual structure, a fourth description of how said manifested conceptual components represented by said plurality of conceptual components included in said refinement of said conceptual structure interact among themselves to perform said plurality of functions of said business, a fifth description of how said business model relates to an organization of said plurality of conceptual components included in said refinement of said conceptual structure, and a sixth description of how said non-functional requirements are addressed by said IT solution and by said manifested conceptual components represented by said plurality of components included in said refinement of said conceptual structure; and generating a diagram representing an overview of said IT solution and including said refinement of said conceptual structure;

computer-usable code for retrieving said diagram representing said overview of said IT solution and including said refinement of said conceptual structure and computer-usable code for generating a documentation that includes said diagram and said description of said plurality of operational concepts;

computer-usable code for developing said architecture and said design of said IT solution by said one or more IT stakeholders based on said developed conceptual model and said documentation that includes said diagram representing said overview of said IT solution and said description of said plurality of operational concepts, wherein said description of said plurality of operational concepts included in said documentation that is a basis for said architecture and said design of said IT solution indicates said interactions among said manifested conceptual components to perform said plurality of functions of said business; and computer-usable code for generating, by said one or more IT stakeholders, a second documentation of said architecture and said design of said IT solution.

8. The program product of claim 7, wherein said third description of information management needs of said manifested conceptual components is independent of any technology used to implement said IT solution.

9. The program product of claim 7, wherein said computer-usable code for generating said description of said plurality of operational concepts includes computer-usable code for generating said second description of said plurality of functions, said one or more internal processes, and said one or more algorithms supported by said manifested conceptual components, wherein said computer-usable code for generating said second description of said plurality of functions includes:

computer-usable code for describing a purpose of a function of said plurality of functions;

computer-usable code for describing one or more inputs and one or more outputs of said function;

computer-usable code for describing an operation of an internal process of said one or more internal processes for performing said function;

computer-usable code for describing one or more information management requirements of said function; and computer-usable code for describing an operation of said function, said operation of said function based on one or more interactions of a manifested conceptual component of said manifested conceptual components with one or more other manifested conceptual components of said manifested of conceptual components.

10. The program product of claim 7, wherein said computer-usable code for refining said conceptual structure includes computer-usable code for generating said plurality of conceptual components as a plurality of modular representations that are independent of any technology used to implement said one or more IT systems represented by said plurality of conceptual components.

11. A process for supporting computing infrastructure, said process comprising providing at least one support service for at least one of creating, integrating, hosting, maintaining, and deploying computer-readable code in a computing system, wherein the code in combination with the computing system is capable of performing a method of developing an information technology solution via development of a conceptual model, said method comprising:

defining, by one or more business stakeholders associated with a business, a plurality of requirements of an information technology (IT) solution owned by said business, wherein said requirements indicate a plurality of functions of said business to be supported by said IT solution;

said one or more business stakeholders and one or more IT stakeholders associated with said business developing a conceptual model by developing a conceptual structure and subsequently developing a plurality of operational concepts, said conceptual model including said conceptual structure and said plurality of operational concepts and providing a representation of said IT solution, said conceptual structure including a plurality of conceptual components, said plurality of conceptual components being icons, forms, shapes and/or figures determined by outlines that modularly represent one or more IT systems, one or more hardware components of said one or more IT systems and one or more software components of said one or more IT systems, said one or more IT systems, said one or more hardware components and said one or more IT systems being manifestations (manifested conceptual components) of said plurality of conceptual components in an implementation of said IT solution, and said plurality of operational concepts indicating interactions among said manifested conceptual components to perform said plurality of functions of said business, wherein said developing said conceptual structure includes:

defining said conceptual structure based on a functional analysis of said plurality of functions of said business by said one or more business stakeholders and said one or more IT stakeholders; and subsequent to said defining said conceptual structure, refining said conceptual structure by:

refining said conceptual structure based on a first analysis of interactions of one or more users with said IT solution;

refining said conceptual structure based on a second analysis of a business model of said business;

refining said conceptual structure based on a third analysis of how said manifested conceptual components interact with each other to support a business operational model of said business, said business operational model being a description by said one or more business stakeholders of how said business operates to attain one or more operational goals of said business;

refining said conceptual structure based on a fourth analysis of one or more internal processes and one or more algorithms, said one or more internal processes associated with an operation of a set of manifested conceptual components included in said manifested conceptual components and with interactions therebetween, and said one or more algorithms associated with said operation of said set of manifested conceptual components and with said interactions therebetween;

refining said conceptual structure based on a fifth analysis of one or more requirements for communication among said manifested conceptual components, between said IT solution and one or more systems of said IT solution, and between said IT solution and one or more systems external to said IT solution;

refining said conceptual structure based on a sixth analysis of one or more requirements for capturing, storing, retrieving and managing information internal to said one or more systems of said IT solution; and refining said conceptual structure based on a seventh analysis of non-functional requirements of said IT solution, wherein a result of said refining said conceptual structure is a refinement of said conceptual structure, wherein said refinement includes a new conceptual component added to said plurality of conceptual components, wherein said refinement further includes a partition of a conceptual component of said plurality of conceptual components into two or more conceptual components that are added to said plurality of conceptual components and/or an aggregation of at least two conceptual components of said plurality of conceptual components into a new composite conceptual component added to said plurality of conceptual components, wherein said subsequently developing said plurality of operational concepts includes:

prior to developing an architecture and a design of said IT solution, generating a description of said plurality of operational concepts based on said refinement of said conceptual structure, said description including:

a first description of said plurality of conceptual components included in said refinement of said conceptual structure, a second description of said plurality of functions, said one or more internal processes, and said one or more algorithms supported by said manifested conceptual components represented by said plurality of conceptual components included in said refinement of said conceptual structure, a third description of information management needs of said manifested conceptual components represented by said plurality of conceptual components included in said refinement of said conceptual structure, a fourth description of how said manifested conceptual components represented by said plurality of conceptual components included in said refinement of said conceptual structure interact among themselves to perform said plurality of functions of said business, a fifth description of how said business model relates to an organization of said plurality of conceptual components included in said refinement of said conceptual structure, and a sixth description of how said non-functional requirements are addressed by said IT solution and by said manifested conceptual components represented by said plurality of components included in said refinement of said conceptual structure; and generating a diagram representing an overview of said IT solution and including said refinement of said conceptual structure;

a computing system retrieving said diagram representing said overview of said IT solution and including said refinement of said conceptual structure and generating a documentation that includes said diagram and said description of said plurality of operational concepts;

developing said architecture and said design of said IT solution by said one or more IT stakeholders based on said developed conceptual model and said documentation that includes said diagram representing said overview of said IT solution and said description of said plurality of operational concepts, wherein said description of said plurality of operational concepts included in said documentation that is a basis for said architecture and said design of said IT solution indicates said interactions among said manifested conceptual components to perform said plurality of functions of said business; and generating, by said one or more IT stakeholders, a second documentation of said architecture and said design of said IT solution.

12. The process of claim 11, wherein said third description of information management tools of said manifested conceptual components is independent of any technology used to implement said IT solution.

13. The process of claim 11, wherein said generating said description of said plurality of operational concepts includes generating said second description of said plurality of functions, said one or more internal processes, and said one or more algorithms supported by said manifested conceptual components by:

describing a purpose of a function of said plurality of functions;

describing one or more inputs and one or more outputs of said function;

describing an operation of an internal process of said one or more internal processes for performing said function;

describing one or more information management requirements of said function; and describing an operation of said function, said operation of said function based on one or more interactions of a manifested conceptual component of said manifested conceptual components with one or more other manifested conceptual components of said manifested of conceptual components.

14. The process of claim 11, wherein said refining said conceptual structure includes generating said plurality of conceptual components as a plurality of modular representations that are independent of any technology used to implement said one or more IT systems represented by said plurality of conceptual components.

* * * * *